US009427529B2

(12) United States Patent
Cabiri

(10) Patent No.: US 9,427,529 B2
(45) Date of Patent: Aug. 30, 2016

(54) SAFEGUARD MECHANISM FOR AUTOINJECTOR NEEDLE

(71) Applicant: MEDIMOP Medical Projects Ltd., Ra'anana (IL)

(72) Inventor: Oz Cabiri, Macabim-Reut (IL)

(73) Assignee: MEDIMOP MEDICAL PROJECTS LTD., Ra'Anana (IL)

(*) Notice: Subject to any disclaimer, the term of this patent is extended or adjusted under 35 U.S.C. 154(b) by 0 days.

(21) Appl. No.: 14/186,403

(22) Filed: Feb. 21, 2014

(65) Prior Publication Data
US 2014/0171881 A1 Jun. 19, 2014

Related U.S. Application Data

(63) Continuation-in-part of application No. 14/096,977, filed on Dec. 4, 2013, which is a continuation-in-part of application No. 13/063,236, filed as application No. PCT/US2009/056778 on Sep. 14, 2009, now Pat. No. 8,617,126.

(60) Provisional application No. 61/884,597, filed on Sep. 30, 2013, provisional application No. 61/192,198, filed on Sep. 15, 2008.

(51) Int. Cl.
*A61M 5/00* (2006.01)
*A61M 5/32* (2006.01)
*A61M 5/142* (2006.01)
*A61M 5/20* (2006.01)

(52) U.S. Cl.
CPC ....... *A61M 5/3213* (2013.01); *A61M 5/14248* (2013.01); *A61M 5/20* (2013.01); *A61M 5/3287* (2013.01); *A61M 5/3204* (2013.01); *A61M 2005/14252* (2013.01); *A61M 2207/00* (2013.01); *Y10T 29/49826* (2015.01)

(58) Field of Classification Search
CPC .. A61M 2207/00; A61M 5/20; A61M 5/326; A61M 5/3287; A61M 5/3213; A61M 5/14248; A61M 5/3204
See application file for complete search history.

(56) References Cited

U.S. PATENT DOCUMENTS 4,195,636 A 4/1980 Behnke
4,222,380 A 9/1980 Terayama
(Continued)

FOREIGN PATENT DOCUMENTS

EP 0 526 986 A1 2/1993
EP 1930038 A2 6/2008
(Continued)

OTHER PUBLICATIONS

U.S. Appl. No. 61/192,198, filed Sep. 15, 2008.
(Continued)

Primary Examiner — Rebecca E Eisenberg
(74) Attorney, Agent, or Firm — Panitch Schwarze Belisario & Nadel LLP

(57) ABSTRACT

In accordance with some embodiments of the present invention there is provided a method of preparing a compound device for use. The device may include a sealed component and an active outer surface. The outer surface may be protected by a surface cover. Preparing the device may include activating the active outer surface by removing the surface cover and exposing an internal portion of the sealed component to the exterior of the device by unsealing the sealed component and synchronizing the activating and said unsealing using a coupler attached to the surface cover and the sealed component.

23 Claims, 19 Drawing Sheets

(56) References Cited

U.S. PATENT DOCUMENTS

| | | | |
|---|---|---|---|
| 4,270,537 | A | 6/1981 | Romaine |
| 4,403,987 | A | 9/1983 | Gottinger |
| 4,781,688 | A | 11/1988 | Thoma et al. |
| 5,190,521 | A | 3/1993 | Hubbard et al. |
| 5,478,315 | A | 12/1995 | Brothers et al. |
| 5,662,678 | A | 9/1997 | Macklin |
| 5,766,186 | A | 6/1998 | Faraz et al. |
| 6,200,296 | B1 | 3/2001 | Dibiasi et al. |
| 6,743,211 | B1 | 6/2004 | Prausnitz et al. |
| 7,060,054 | B2 | 6/2006 | Nissels |
| 7,291,159 | B2 | 11/2007 | Schmelzeisen-Redeker et al. |
| 7,740,600 | B2 | 6/2010 | Slatkine et al. |
| 2002/0022798 | A1 | 2/2002 | Connelly et al. |
| 2003/0229308 | A1 | 12/2003 | Tsals et al. |
| 2004/0030353 | A1 | 2/2004 | Schmelzeisen-Redeker et al. |
| 2005/0033234 | A1 | 2/2005 | Sadowski et al. |
| 2005/0101912 | A1 | 5/2005 | Faust et al. |
| 2006/0293722 | A1 | 12/2006 | Slatkine et al. |
| 2007/0270745 | A1 | 11/2007 | Nezhat et al. |
| 2009/0043245 | A1 | 2/2009 | Nguyen |
| 2009/0093792 | A1 | 4/2009 | Gross et al. |
| 2009/0118662 | A1 | 5/2009 | Schnall |
| 2010/0185148 | A1 | 7/2010 | Gillespie, III et al. |
| 2010/0286714 | A1 | 11/2010 | Gyrn et al. |
| 2011/0040280 | A1 | 2/2011 | Ijitsu et al. |
| 2011/0166509 | A1 | 7/2011 | Gross et al. |
| 2014/0088509 | A1 | 3/2014 | Sonderegger et al. |
| 2014/0249502 | A1 | 9/2014 | Nie |

FOREIGN PATENT DOCUMENTS

| | | |
|---|---|---|
| EP | 2316510 A2 | 5/2011 |
| EP | 2468340 A1 | 6/2012 |
| EP | 2468342 A1 | 6/2012 |
| EP | 2578188 A1 | 4/2013 |
| WO | 03103750 A1 | 12/2003 |
| WO | 2006/016364 A2 | 2/2006 |
| WO | 2006/069380 A1 | 6/2006 |
| WO | 2008034743 A1 | 3/2008 |
| WO | 2012000836 A1 | 1/2012 |
| WO | 2012134588 A1 | 10/2012 |
| WO | 2012145685 A1 | 10/2012 |

OTHER PUBLICATIONS

Int'l Search Report issued on Aug. 11, 2010 in Int'l Application No. PCT/US2009/056778.

Int'l Preliminary Report on Patentability issued Mar. 15, 2011 in Int'l Application No. PCT/US2009/056778.

Office Action issued Oct. 17, 2012 in U.S. Appl. No. 13/063,236.

Office Action issued May 23, 2013 in U.S. Appl. No. 13/063,236.

U.S. Appl. No. 14/096,977 by Cabiri, filed Dec. 4, 2013.

Int'l Search Report and Written Opinion issued Mar. 2, 2015 in Int'l Application No. PCT/US2014/058446.

Int'l Search Report and Written Opinion issued May 27, 2015 in Int'l Application No. PCT/US2014/058456.

Office Action issued Jul. 2, 2015 in U.S. Appl. No. 14/096,977 by Cabiri.

Int'l Search Report and Written Opinion issued Dec. 12, 2014 in Int'l Application No. PCT/US2014/058433.

Office Action issued Jan. 4, 2016 in U.S. Appl. No. 14/096,977 by Cabiri.

Int'l Preliminary Examination Report issued Apr. 14, 2016 in Int'l Application No. PCT/US2014/058446.

Int'l Preliminary Examination Report issued Apr. 14, 2016 in Int'l Application No. PCT/US2014/058433.

Int'l Preliminary Examination Report issued Apr. 14, 2016 in Int'l Application No. PCT/US2014/058456.

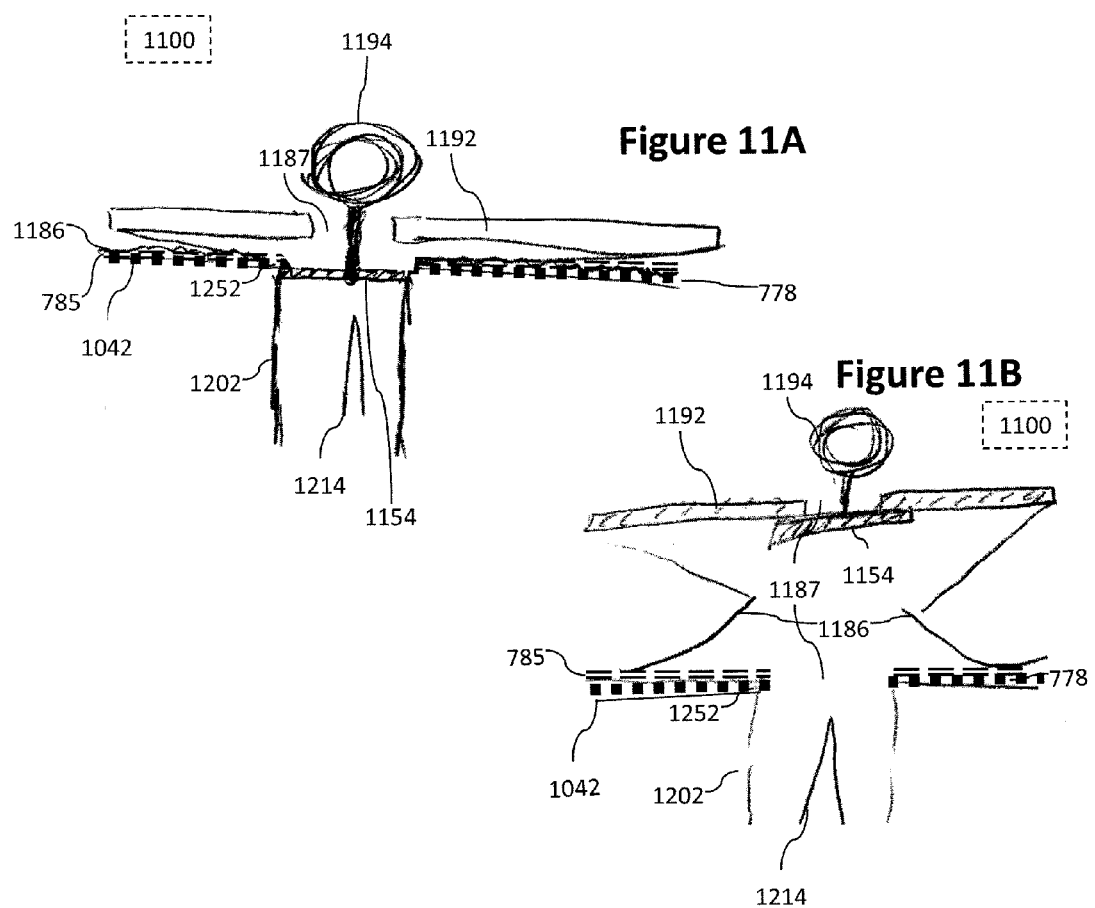

SAFEGUARD MECHANISM FOR AUTOINJECTOR NEEDLE

RELATED APPLICATIONS

This application claims the benefit of priority under 35 USC §119(e) of U.S. Provisional Patent Application No. 61/884,597 filed Sep. 30, 2013, and is a Continuation-In-Part of patent application Ser. No. 14/096,977 filed Dec. 4, 2013, which is a Continuation-In-Part of U.S. application Ser. No. 13/063,236 filed Mar. 10, 2011, which is a Section 371 of International Application No. PCT/US09/56778 filed Sep. 14, 2009, which claims priority to U.S. Provisional Application No. 61/192,198 filed Sep. 15, 2008. The contents of all of the above applications are incorporated by reference as if fully set forth herein.

FIELD AND BACKGROUND OF THE INVENTION

The present invention, in some embodiments thereof, relates to a composite medical and, more particularly, but not exclusively, to synchronized preparing for use of internal and external components of a composite medical device.

U.S. Patent Application Publication No. 2011/0098656 to Burnell discloses an injection device having a housing that receives a syringe having a sealed boot that covers its needle. The syringe is biased by a return spring from an extended position in which the needle extends from the housing through an exit aperture to a retracted position in which it does not. A drive spring acts via a drive to advance the syringe from its retracted position to its extended position and discharge its contents through the needle and a return the spring, brought into play when the drive has reached a nominal return position, restores the syringe to its retracted position. A releasable locking mechanism retains the syringe in its retracted position. A sleeve projects from the exit aperture and can be depressed to release the locking mechanism. A removable threaded cap closes the housing, covers the exit aperture and the sleeve, thus preventing the locking mechanism from being released, and engages the boot on the syringe. When the cap is removed, it takes the boot with it, no longer closes the exit aperture and no longer prevents the locking mechanism from being released. Then, the locking mechanism can be released and the injection cycle begun.

U.S. Patent Application Publication No. 2013/0310753 to Cabiri discloses a method for selectively powering a battery-operated drug-delivery device, the device having a battery and a battery circuit, the method comprising: providing a battery isolator in a first position whereat it interrupts a battery circuit, whereby no power is provided to the device; and activating a fastening mechanism configured for fastening the device to a user, the activating causing the battery circuit to be uninterrupted by the isolator, such that power is provided to the device. Additionally, there is provided a selectively powered battery-operated drug-delivery device, comprising: a selectively-removable isolator disposed in a first position whereat it interrupts a battery circuit; the isolator movable to a second position whereat the battery circuit is uninterrupted by the isolator; and a mechanism for fastening the device to a user, activation of the fastening mechanism moving the isolator from the first position to the second position.

U.S. Patent Application Publication No. 2012/0323183 to Peterson discloses a drug delivery device, including a body having a needle opening and a reservoir disposed therein for containing a medicament, and an injection needle for penetrating the skin of a patient, the needle providing a path for the medicament between the reservoir and the patient, and selectively protruding from the body through the needle opening. The device also includes safety means for automatically retracting the needle within the body and covering the needle opening upon removal of the device from the patient.

U.S. Patent Application Publication No. 20050049561 to Hommann discloses a device for administering an injectable product including a casing, an injection mechanism including an injection needle pointing in an insertion direction, and a protective cap for the injection needle wherein, in one embodiment, the administering device includes a removing device for removing the protective cap from the injection needle and, in another embodiment, the administering device includes a needle protecting sleeve shiftable generally in alignment with the casing and generally between a front position, advanced relative to the casing, for protecting the injection needle and to a rear position, retracted relative to the casing, for inserting the injection needle into a tissue. In one embodiment, the needle protecting sleeve is prevented from moving completely into the rear position by a lock when the protective cap is protecting the injection needle.

Additional background art includes International Patent Application Publication No. WO 2001052925 to Sterling Medivations Inc.

SUMMARY OF THE INVENTION

According to an aspect of some embodiments of the present invention there is provided a compound device having an interior volume and an exterior surface including: a wall located between the interior volume and an exterior of the compound device; a protected component surrounded by an enclosure, the enclosure at least partially located in the interior volume; a seal for closing the enclosure and for isolating the protected component from the wall; an active area formed on at least a portion of the exterior surface;

a cover shielding the active area from the exterior; and, a coupler attaching the seal to the cover, the coupler synchronizing removal of the cover and unsealing of the enclosure.

According to some embodiments of the invention, the compound device further includes an opening in the wall exposing the enclosure to the exterior.

According to some embodiments of the invention, the active area is adjacent to the opening.

According to some embodiments of the invention, the coupler connects the seal to the cover via the opening.

According to some embodiments of the invention, the active area includes an adhesive.

According to some embodiments of the invention, the protected component includes a hypodermic needle.

According to some embodiments of the invention, the seal includes a needle protective sleeve.

According to some embodiments of the invention, the compound device further includes an opening in the wall exposing the enclosure to the exterior and the hypodermic needle is directed to protrude through the opening in the wall.

According to some embodiments of the invention, the coupler converts a movement away from the exterior surface into a peeling force on the cover.

According to some embodiments of the invention, the coupler is connected to an edge of the cover.

According to some embodiments of the invention, a volume of the enclosure is smaller than a volume of the interior volume.

According to an aspect of some embodiments of the present invention there is provided a method of preparing a device for use, the device including an active outer surface and a protected component isolated from a wall of the device by a sealed enclosure; the active outer surface protected by a surface cover, the method including: activating the active outer surface by removing the surface cover; exposing the protected component to the wall of the device by unsealing the sealed enclosure and synchronizing the activating and the unsealing using a coupler attached to the surface cover and the sealed enclosure.

According to some embodiments of the invention, the activating includes peeling the surface cover from the active outer surface.

According to some embodiments of the invention, the method further includes pulling the coupler away from the surface cover to form a space prior to the peeling.

According to some embodiments of the invention, the protected component includes a hypodermic needle, and the peeling force is applied on an edge of the cover.

According to some embodiments of the invention, the unsealing includes pulling a needle protective sleeve along an axis of a needle.

According to some embodiments of the invention, the protected component includes a hypodermic needle, the method further including: projecting the hypodermic needle through an opening in the wall.

According to some embodiments of the invention, the active surface is adjacent to the opening.

According to an aspect of some embodiments of the present invention there is provided a method of removing a cap and peeling a cover from a surface including: providing a coupler joining the cap to the cover; pulling the cap and a portion of the coupler joined thereto away from the surface and converting of the pulling force on the coupler to a peeling force on the cover of the surface.

According to some embodiments of the invention, the method further includes applying the peeling force on an adhered edge of the cover.

According to some embodiments of the invention, the cap includes a needle protective sleeve and the pulling is along an axis of a needle.

According to some embodiments of the invention, the cap protects a sterility of a hypodermic needle and the method further includes: projecting the hypodermic needle through an opening in the surface.

According to an aspect of some embodiments of the present invention there is provided a method of preparing a device for use including: supplying a component of the device sealed by a seal; protecting an external surface of the device with a cover; joining the seal to the cover such that breaking seal and removing the cover are synchronized.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 11A-B illustrate a cross sectional views an alternative enabling assembly of a patch injector according to an embodiment of the current invention;

DESCRIPTION OF SPECIFIC EMBODIMENTS OF THE INVENTION

Figure 1A:
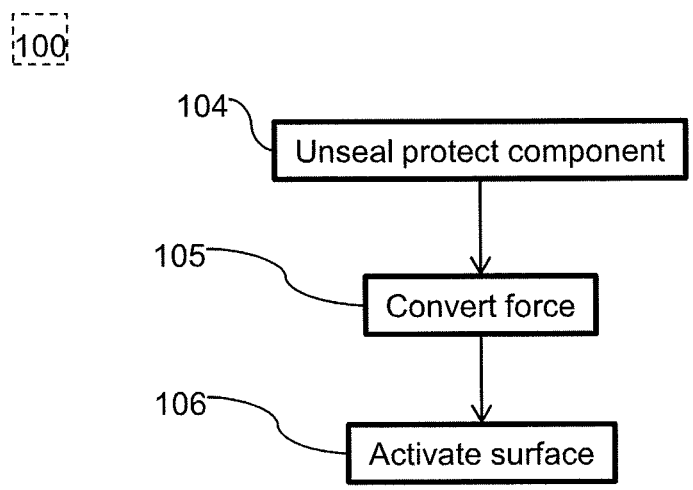
FIG. 1A is a flowchart illustrating a method of enabling a compound device according to an embodiment of the present invention.

The present invention, in some embodiments thereof, relates to a composite medical and, more particularly, but not exclusively, to preparing a composite medical device for use.

Overview

1 Activating a Surface and Unsealing an Isolated Zone

An aspect of some embodiments of the present invention relates to enabling a compound device requiring peeling a cover for example from an active surface and exposing a protected component isolated from the surface. The peeling and unsealing may optionally be synchronized. For example, the surface may include a non-sterile or low-level sterile adhesive to be adhered to the skin of a patient and the protected component may include a highly sterile implement for insertion into tissue of the patient. For example, the protected component may be in an isolated enclosure located behind an opening in the adhesive surface. An adhesive cover may be joined through the opening to a seal of the isolated enclosure. Optionally, peeling away the adhesive cover may unseal the enclosure exposing the protected component to the opening. In some embodiments the adhesive surface may be sterile. Optionally the adhesive cover may protect the sterility of the adhesive.

2 Coupler to Peel a Surface Cover with an Axial Force

An aspect of some embodiments of the present invention relates to an apparatus that converts a movement away from a surface to peeling movement along the surface. For example a device may optionally include a cap that is removed by pulling linearly away from the body of the device. The device may optionally include a surface cover that may be removed from a surface by peeling. In some embodiments, a coupler may connect between the cap and the surface cover. Optionally, while the cap is being pulled off, the coupler may convert the pulling force on the cap to a peeling force on the surface cover. In some embodiments, the coupler may apply a force that tears a sealed packaging. For example, the sealed packaging may protect a sterility of the adhesive. Optionally the peeling force may be applied to an edge of the surface cover. For example the coupler may be flexible and/or a hinged and/or may be anchored to an edge of the surface cover. In some embodiments, the coupler may include slack that allows limited movement of the cap before the commencement of peeling. For example, the slack may allow movement of the cap to a certain distance away from the body for example to get an improved leverage on the peeling before peeling begins.

3 Application to a Medical Injector

An aspect of some embodiments of the present invention relates to a mechanism to synchronize peeling an adhesive cover and exposing needle an autoinjector. For example the safety cap may include a needle protector remover. Optionally, safety cap and/or the needle protector remover may be attached to an adhesive cover. The safety cover may optionally protect the device from uncontrolled early activation. As the safety cap is pulled away the pulling force may be transferred to a peeling force at one or more edges of the adhesive cover.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

EXEMPLARY EMBODIMENTS

1 Unsealing a Protected Component and Activating a Surface

Referring now to the drawings, FIG. 1a illustrates a method of synchronizing unsealing of a protected component and peeling of a surface cover according to an embodiment 100 of the present invention. For example a protected component may be unsealed 104 (for example by removing and/or breaking and/or melting a seal [for example seal 191 of FIG. 1b]). For example, the unsealing may be by means of application of a linear and/or twisting force to the sealed component. The unsealing force may be converted 105 to an activating 106 energy on an active surface of the device.

Figure 1B:
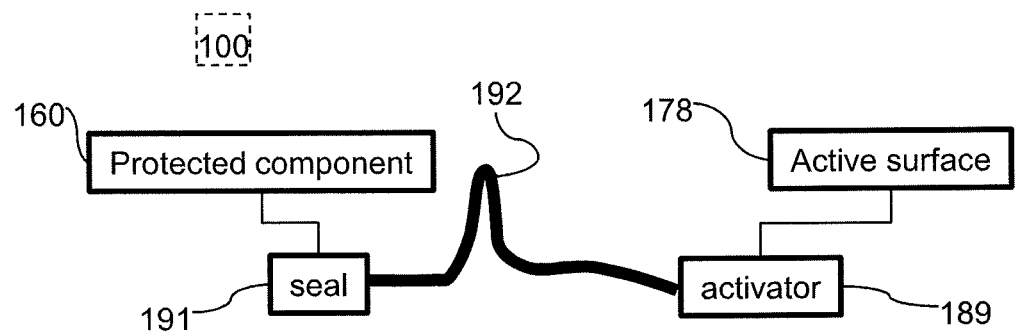
FIG. 1B is a schematic block diagram of a compound device according to an embodiment of the present invention.

Referring now to the drawings, FIG. 1b is a block diagram illustration of a system for synchronizing unsealing 104 of a protected component and activation 106 of a surface according to an embodiment 100 of the present invention. For example, some embodiments may include a seal 191 for isolating one or more protected components 160 and/or an activator 189 for an active surface 178. Optionally seal 191 and activator 189 may be joined by a coupler 192. Coupler 192 may convert 105 an energy unsealing 104 seal 191 to activate 106 of an active surface. In some embodiments coupler 192 may include slack, for example a fold and/or wrinkle and/or an elasticity which allows some individual movement of seal 191 and/or activator 189 before synchronized movement begins.

2 Method of Injecting a Drug

Figure 2:
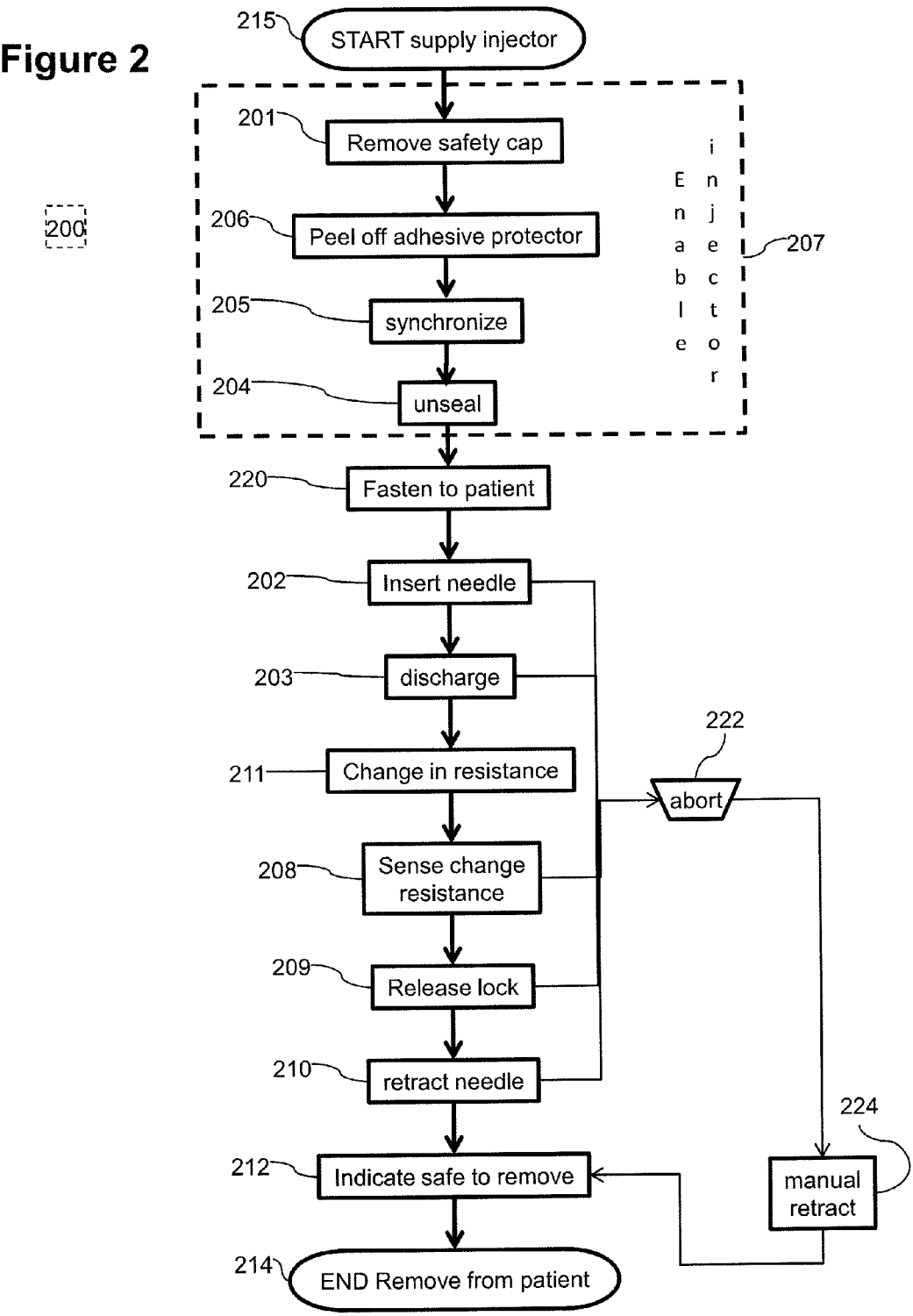
FIG. 2 is a flowchart illustrating a method of enabling a compound device according to an embodiment of the present invention.

Referring now to the drawings, FIG. 2 illustrates a method of injecting a drug according to an embodiment 200 of the present invention. In exemplary embodiment 200, a protected component (for example a hypodermic needle) is optionally kept isolated and sterile, for example, by a needle protector (for example a needle protective sleeve). The needle protector may be unsealed 204 right before use, for example by pulling it away from the needle. In the exemplary method, an active surface (an adhesive contact surface) optionally holds the injector stable while a drug is dispensed to a patient. The active surface may be activated before use for example by peeling 206 away an adhesive cover. A coupler (for example a safety cap) may optionally join the adhesive cover to the needle protector. The coupler may optionally synchronize 205 unsealing 204 of the needle protector and peeling 206 the adhesive cover. For example, the safety cap may be attached to the needle protector and/or attached to an edge of the adhesive cover for example by extenders. Linearly pulling the safety cap away from the injector may unseal 204 the needle protector (for example by pulling the cap away from the needle) and/or unfurl the extenders and/or peel 206 the adhesive cover from the adhesive surface. Optionally a sealed sterile adhesive may be connected to the active surface. Unsealing 204 may include unsealing the adhesive (for example by tearing a protective packaging).

In exemplary embodiment 200 a user (for example a patient and/or a medical aid in home care) may be supplied 215 with an autoinjector ready to administer a medicine.

The user may optionally enable 207 the injector. For example, enabling the injector may include removing 201*a* a safety cap from the injector. Removing 201 the cap may optionally be synchronized 205 with unsealing 204 a protected component of the injector. For example the safety cap may be attached to a sterile needle protector. Removing 201 the safety cap may optionally remove the sterility protector from a needle. Removing 201 the cap may optionally automatically peel 206 an adhesive cover from an adhesive. The single intuitive act of removing 201 the safety cap may, optionally, completely enable 207 the injector for use with one action, for example, by activating the adhesive surface and opening a path for the needle to be inserted in the patient simultaneously.

In some embodiments, once the injector is enabled, it may optionally be fastened 220 to a patient (who may be the user). The adhesive may optionally serve to stabilize the injector on the skin of a patient during injection.

In some embodiments, the user may set off an activation mechanism. The activation mechanism may for example insert 202 the needle into the patient, for example by extending the needle outward. For example, a syringe may be moveably attached to the base. A needle may optionally be rigidly attached to the syringe. For example the syringe may slide linearly along its axis. Sliding the syringe towards the base may cause the needle to protrude beyond the base. For example, part of the needle may pass through an opening in the base and pierce the skin of a patient. The adhesive of the base may hold the skin of the patient steady while the needle pierces the skin. The combination of an adhesive holding the skin and moving the needle to a predetermined position past the base may facilitate the inserting 202 of the needle into the skin to the desired depth.

The needle may optionally be locked in the extended position. Optionally, the needle may be biased to a protected position (for example to retract into a housing of the injector). Alternatively or additionally, the needle may be biased to the unshielded position. Alternatively or additionally, the autoinjector may be supplied with the needle in an extended mode and/or protected by a protector.

At a point during the injection process, an optional manual retraction 224 mechanism may be used to place the injector in a safeguarded mode. For example, when the user decides to abort 222 at a point in the process (for example when he detects some sort of malfunction and/or feels a negative reaction to the medicine) the user may manually retract 224 the needle. Optionally there may be an indicator to indicate 212 whether the needle was automatically retracted 210 and/or whether needle was manually retracted 224. Alternatively or additionally there may be an indicator whether a full dose was administered and/or how much medicine was administered.

Once the needle is inserted 202 into the patient, the injector may optionally begin discharging 203 medicine. For example the medicine may be injected through the needle into the patient. Optionally, discharge 203 may continue until a full dose of the medicine is administered.

In some embodiments, after administration of a full dose of the medicine, there may be a change 211 in resistance to further discharging. For example in a syringe based injector, a plunger may reach the end of the syringe and cease to move increasing resistance. Alternatively or additionally, after discharging the entire dose a transmission may be disconnected (for example a threaded element may pass the end of its threading) reducing resistance. Alternatively or additionally, the change 211 in resistance may result from another cause for example increased resistance due to a full or partial occlusion of a fluid pathway and/or jamming of a mechanical component (for example cross threading of a screw). The change of resistance may optionally be sensed 208 triggering retracting 210 of the needle.

In some embodiments, the needle may be locked in an unshielded state by a force sensitive lock. When the lock senses 208 the change 211 in resistance, it may release 209 the needle which may be retracted 210 to a shielded position.

In some embodiments, a flag may be supplied (for example a LED and/or a changing color indicator) to indicate 212 to the user that the needle has been retracted 210 and/or that the injector can safely be removed 214 from the patient and/or that a fastener has been released. For example, if the injector is adhered to the patient, it may be peeled off and/or a fastener may be released.

3 State Diagram

Figure 3:
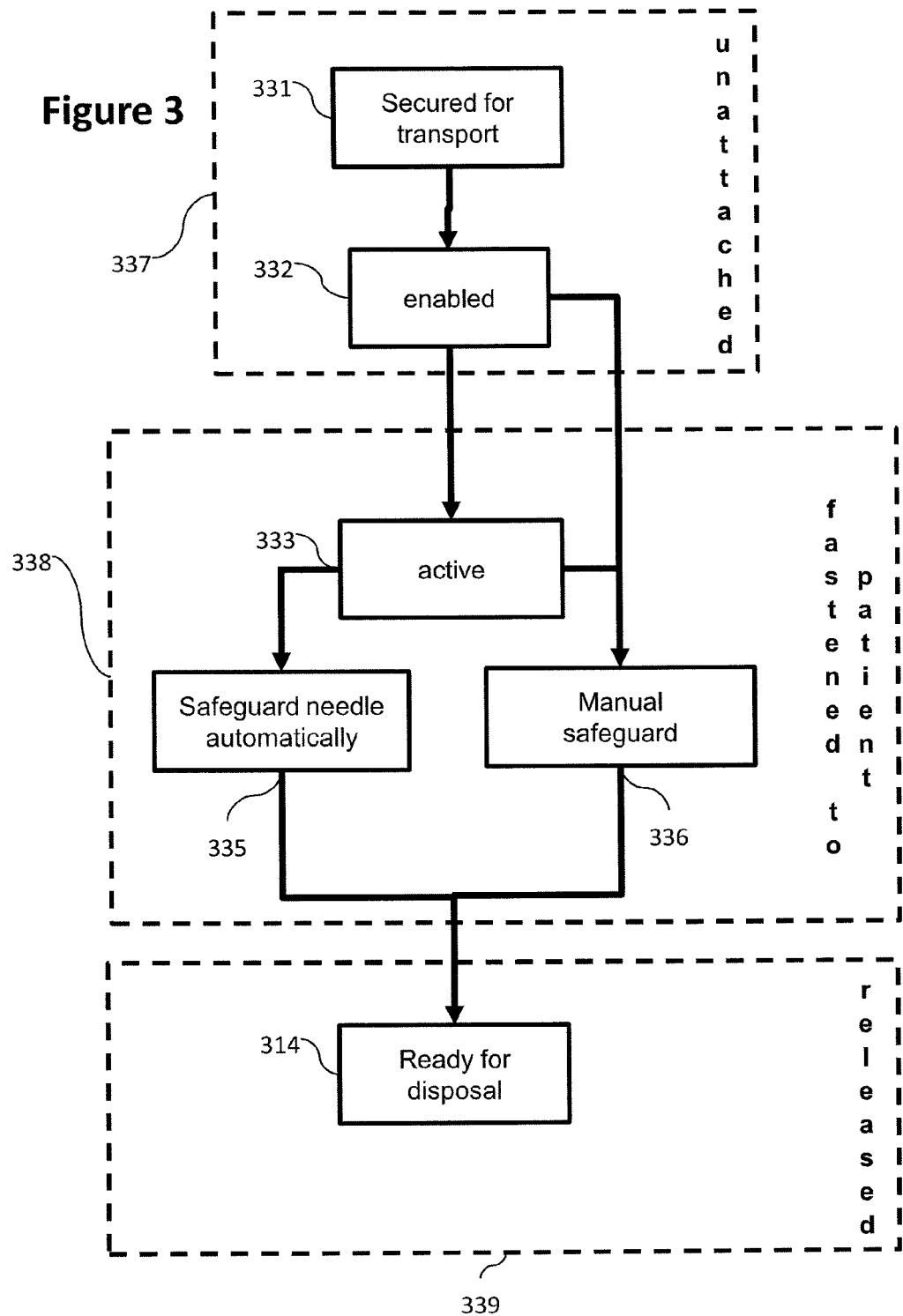
FIG. 3 is a state diagram of an injector according to an embodiment of the present invention.

FIG. 3 is a state diagram of an autoinjector according to an embodiment of the present invention. In some embodiments, an autoinjector may be supplied in an unattached 337 state. While unattached 337 the autoinjector may have a secured 331 state. For example in the secured 331 state the injector may be safe to handle and/or transport. Optionally the injector may have an enabled 332 state. For example, in the enabled 332 state, the injector may be unstable and/or easily activated and/or sensitive parts may be exposed. For example, an injector may be switched from the secured 331 state to the enabled 332 state by removing a safety cap. Removal of the safety cap may optionally be synchronized with removing of a needle sterility seal (for example a needle protector) and/or an adhesive cover.

In the enabled 332 state, a sterile needle may be free to be extended out of an opening of the injector. In the enabled 332 state the needle may be exposed to potential contamination. In the enabled 332 state an adhesive may be ready to be fastened to a patient. In the enabled 332 state the adhesive may be exposed to dirt which may reduce its tackiness.

Once activated the injector may optionally be fastened to a patient. In the fastened 338 state the injector may optionally be activated. For example, while the injector is in the active 333 state, a needle may project from the injector. In some embodiments the injector may be hazardous to handle in the enabled 332 and/or active 333 states.

In some embodiments, after use (optionally whether or not administration of the full dose was successful) the user may want to remove and/or dispose of the autoinjector. In some embodiments, it may be difficult and/or dangerous to remove an injector in the enabled 332 and/or active 333 states. For example, when an injector is fastened to a patient by an adhesive, it may be difficult to remove the needle by pulling the injector away from the skin. Optionally, first a needle may be retracted from the skin into the injector. Subsequently the adhesive may be removal by peeling from the skin. In some embodiments, the injector may automatically be safeguarded 335 for example by retraction of a needle upon completion of injection. Alternatively or additionally, the user may have the option to manually secure the injector into a safeguarded 336 state. For example, the optional manually needle retraction may avoid the situation where a patient may not be able to properly remove the injector due to a malfunction that leaves the injector fastened to the skin with the needle inserted into the patient. During and/or after safeguarding 335, 336 the injector may be removed from the patient.

Optionally, the injector may have a final released state 339, for example wherein the needle is retracted back into the injector and/or the needle tip is shielded and/or the injector has been unfastened from the patient. Optionally one or more indicators may be supplied to indicate the state of the injector and/or the quantity of medicine discharged. Once released, the injector may be in final 314 state (protected from hazards and/or ready for disposal, for example in a municipal waste).

4 Method of Manufacture of an Compound Device

Figure 4:
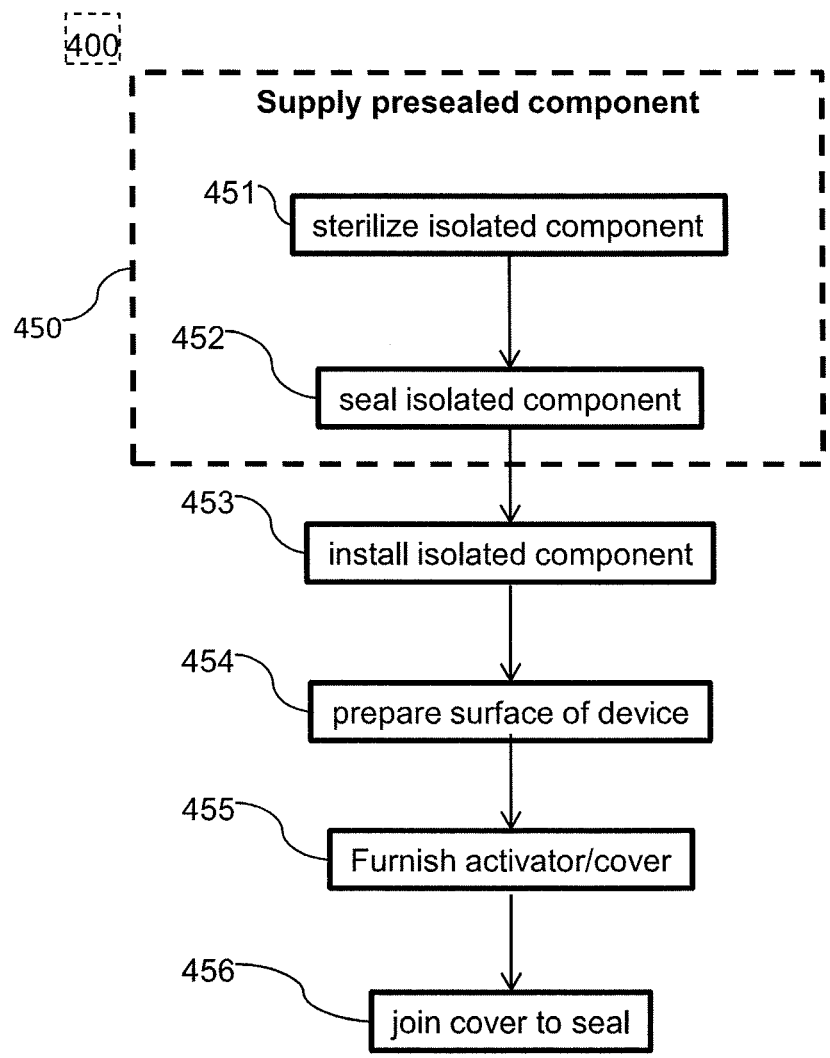
FIG. 4 is a flowchart illustrating a method of manufacture of a compound device according to an embodiment of the present invention.

FIG. 4 is a flow chart illustration of a method of manufacture of a compound device according to an embodiment of the present invention. In some embodiments, a protected component may be installed into a device in a sealed state. The device may optionally include an active surface with an activation mechanism. Optionally, the surface activator may be joined to a seal of the protected component, for example by a coupler. Optionally, the coupler may synchronize unsealing of the protected component and activation of the active surface. For example the method of manufacture illustrated in embodiment 400 of FIG. 4 may optionally be used in manufacturing one, some and/or any of the embodiments of an injector illustrated in the embodiments illustrated herein above and/or below. In some embodiments, an sterile adhesive may be sealed in a protective packaging. The adhesive may for example be attached to a surface in a sterile and/or protected state. Optionally the coupler may be connected to the protective packaging of the adhesive and/or may synchronize opening of the packaging with another act.

In some embodiments an isolated component may be supplied 450 in a presealed state. For example, the presealed component may be a fluid path of a preloaded syringe. Optionally the syringe and/or fluid path may be sterilized 451 and/or preloaded with for example medicine and/or sealed 452 in an aseptic room.

In some embodiments, a protected component may be installed 453 into a device in a sealed state. For example, in some embodiments, a preloaded syringe with a sealed sterile fluid path may optionally be installed 453 into an autoinjector.

In some embodiments, the device may optionally include an active surface with an activation mechanism. The active surface may be prepared 454. For example an autoinjector may include an active surface including an adhesive for attaching to a patient. Preparing 454 the surface may include for example applying the adhesive to the surface.

In some embodiments, the active surface may be furnished 455 with an activation mechanism and/or protective cover. For example, in some embodiments, an adhesive surface may be covered by an adhesive cover and/or activated by removing an adhesive cover.

In some embodiments, the surface cover and/or activator may be joined 456 to the seal of the protected component, for example by a coupler. Optionally, the coupler may synchronize unsealing of the protected component and activation of the active surface. For example removing the surface cover and/or activating the surface may trigger unsealing of the protected component. Alternatively or additionally, unsealing of the protected component may trigger removal of the surface cover and/or activating of the active surface.

5 Stabilized Injector with Double Folded Surface Cover

FIGS. 5A-K illustrate an exemplary embodiment of a compound device including an isolated component protected by a seal and an active surface activated by removing a cover and a coupler joining the seal and the cover for synchronized removal according to some embodiments of the current invention. Optionally, in the exemplary embodiment the surface cover is doubly folded, forming dual extensions that convert a linear unsealing force into a balanced peeling force on opposite edges of adhesion of the surface cover.

Figure 5A:
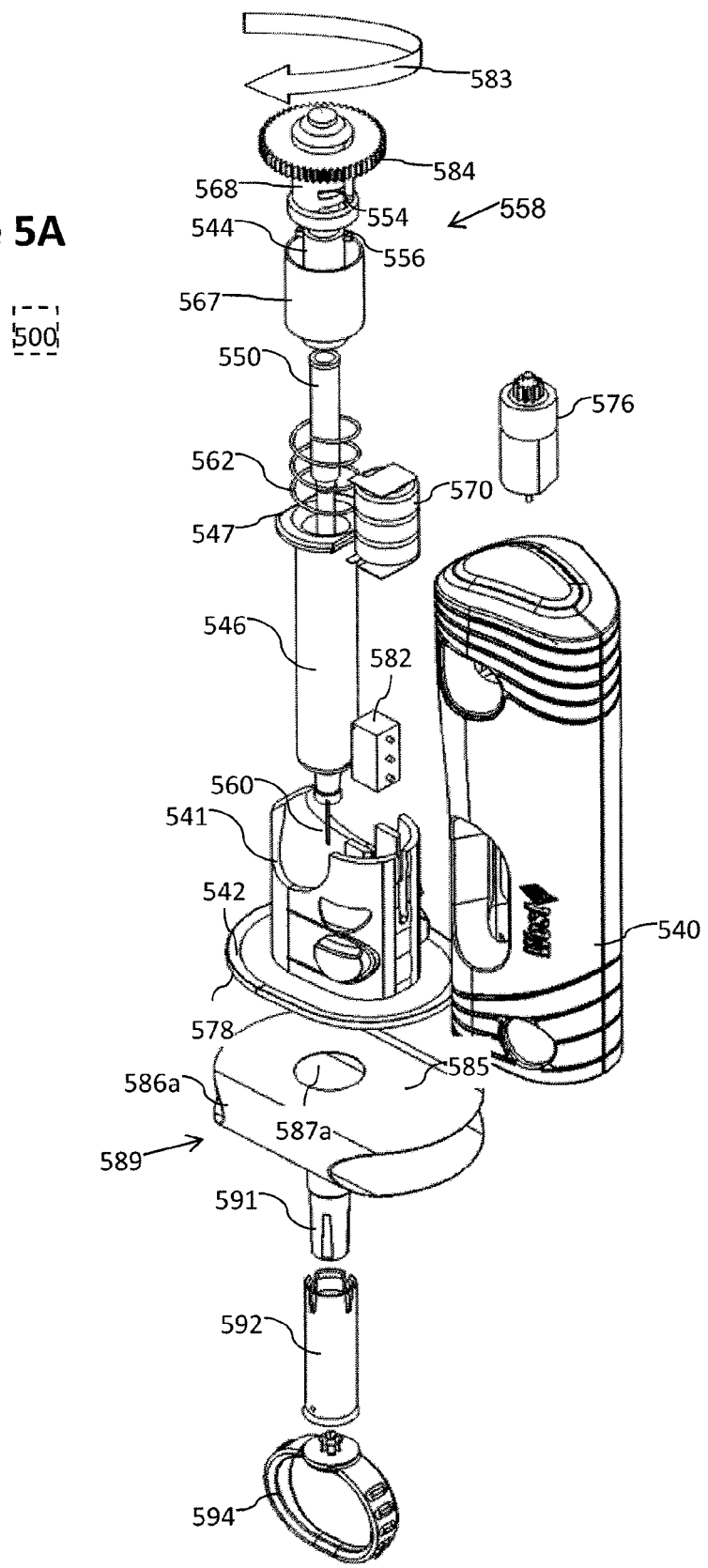
FIG. 5A is an exploded view illustrations of a stabilized injector according to an embodiment of the present invention.

FIG. 5A illustrates an exploded view of a stabilized pen injector according to some embodiments of the current invention. In some embodiments, a prefilled syringe 546 may be installed into the injector. Prior to installation, the syringe may optionally be attached to a sterile fluid path (for example a needle 560). The sterility of fluid path may be protected from contamination by a seal, (for example needle 560 may be isolated from contamination by being enclosed in a needle protector 591 [which is illustrated for example as a needle protective sleeve]). Syringe 546 and/or needle 560 may optionally be installed into injector 500 is a sterile sealed state.

Injector 500 may include for example an adhesive 578 base 542. In some embodiments, an adhesive 578 surface formed on a wall (for example a base 542 of injector 500) may assist a user to hold injector 500 steady on the skin of a patient for an extended period. For example, injector 500 may be used to give injections of volume ranging between 0.5 and 3.0 ml over a time period ranging between 30 sec to 180 sec.

In some embodiments, a coupler (for example safety cap 592) may join needle protector 591 to adhesive cover 589. For example, safety cap 592 may include extenders 586a,b (for example see FIG. 5B) for attaching to adhesive cover 589. Safety cap 592 may optionally be inserted through an opening in adhesive cover 589 (for example opening 587a in the adhered portion 585 and/or openings 587b,c in extenders 586a,b for example see FIG. 5C) and/or an opening 587d (for example see FIG. 5E) in base 542. Extenders 586a,b may optionally be attached to and/or be an integral part of safety cap 592. Optionally a handle 594 may clamp extenders 586a,b to safety cap 592. For example, a coupler for a handle 594 may fit through holes 587b,c in the extenders 586a,b clamping them to safety cap 592.

Optionally injector 500 may be loaded with a standard type syringe 546 and/or hypodermic needle 560. For example, needle 560 may be rigidly connected and/or project from a distal end of syringe 546. Needle 560 may be coaxial with syringe 546. Alternatively or additionally the axis of needle 560 may be parallel to the primary longitudinal axis of syringe 546 but offset therefrom. In some embodiments, injector 500 may include a shield 541 which extends the distal end of a housing 540 of the injector. In some embodiments, a motor switch 582 may be located in shield 541. In the enabled state (before activation), switch 582 is optionally switched off.

In the exemplary embodiment of injector 500 a power supply (for example batteries 570) may optionally supply power to gear motor 576. The motor may optionally turn a threaded assembly and/or a telescoping assembly. For example the threaded assembly may include a rod 550 pushing a plunger 548 [for example see FIG. 5B]). Optionally, syringe 546 may include a flange. For example, flange 547 may have a non-rounded edge which may be held inside injector 500 preventing rotation of syringe 546.

In some embodiments, an injector may include a retraction mechanism. For example, in injector 500, a retraction mechanism 558 is optionally activated by a combination of torque and linear stress. For example the combined torque and linear stress may occur when a plunger (for example plunger 548, see FIG. 5B) is blocked. For example, blockage may occur when plunger 548 reaches the end of injection (and/or for example due to an occlusion of needle 560).

In some embodiments, during drug discharge a motor (for example motor 576) rotates transmission 584 in the direction of arrow 583. Transmission 584 may optionally be rigidly connected to and/or integrally molded with an inner sleeve 568. Rotating transmission 584 may also rotate inner sleeve 568. A pin 556 optionally protrudes from a driver 544 into a nearly horizontal portion of a slot 554 in sleeve 568. In some embodiments, while pin 556 is in the horizontal portion of slot 554, driver 544 is prevented from moving longitudinally with respect to inner sleeve 568. In some embodiments syringe 546 is supported (from moving proximally) by driver 544.

In some embodiments, when there is a strong linear force on driver 544 in the proximal direction and/or there is a strong torque on sleeve 568 in the direction of arrow 583, pin 556 slides out of the horizontal portion of slot 554 into a longitudinal portion of slot 554. In longitudinal portion of slot 554 pin 556 may slide longitudinally (in the proximal direction). A geometry of pin 556 and/or an interference element may optionally be chosen to achieve a desired resistance to movement. For example, pin 556 and/or the interference element may have a squared side, a flat side, a rounded side etc.

In some embodiments, a spring (for example spring 562) biases syringe 546 in the proximal direction. For example spring 562 may apply a proximal force to flange 547. Optionally another biasing element may be used in place of spring 562. For example, a biasing element may include a stretched element (for example a rubber band and/or a twisted elements and/or a deflected plastic element). Alternatively or additionally, syringe 546 may be moved up and down by a motor and/or a pulley and/or a screw and/or a hydraulic element and/or the like.

Optionally when pin 556 enters the longitudinal portion of slot 554, spring 562 may optionally push syringe 546 and/or outer sleeve 567 and/or needle 560 and/or driver 544 and/or pin 556 proximally, retracting needle 560. Optionally, needle 560 may be held in the retracted position by spring 562. Alternatively or additionally a locking mechanism may be included to lock needle 560 in the retracted position, for example, a one way catch and/or an interference element may lock against syringe 546 as it is retracted and/or against pin 556 in slot 554. Optionally, in injector 500 driver 544 includes two molded plastic telescoping pieces. One piece is optionally integrally molded with outer sleeve 567. Optionally, sleeve 567 and/or driver 544 may be made as a single piece and/or multiple parts. They may be formed of plastic and/or another material and/or they may be molded and/or formed by another process.

Figure 5B:
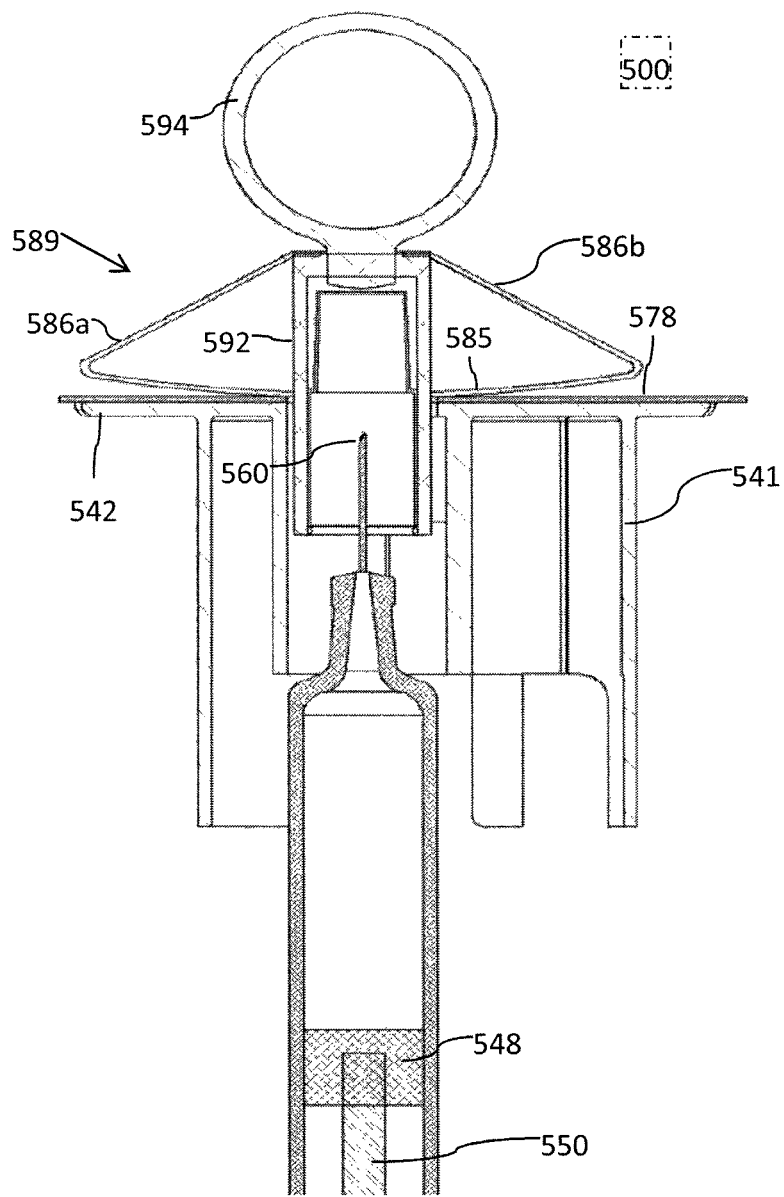
FIG. 5B is a cross sectional illustration of an enabling assembly for a compound device according to an embodiment of the present invention.

FIG. 5B illustrates peeling adhesive cover 589 from an adhesive 578 according to an embodiment of the present invention. In embodiment 500 safety cap 592 may optionally serve as a peeler for an adhesive cover 589. For example, safety cap 592 is attached to extenders 586a,b. Extenders 586a,b may optionally connect safety cap 592 to an edge of adhered portion 585 of adhesive cover 589. For example, in embodiment 500 extenders 586a,b may be formed from adhesive cover 589. Alternatively or additionally, extenders may be hinged and/or flexible extensions to safety cap 592. Optionally, pulling handle 594 which may optionally be located at the center of safety cap 592 does not pull adhesive cover 589 directly away from the whole surface of the adhesive 578 all at once (an act that might require a large force to overcome the sticking force over a large surface). When handle 594 at is pulled, safety cap 592 may optionally move away from adhesive cover 589. Extenders 586a,b may unfurl, unfold, stretch and/or bend to allow a certain distance to build up. Then they may optionally convert the linear force away from base 542 to a peeling force at the edge of adhesion of adhesive cover adhesive cover. The peeling force may optionally be along the surface of base 542 and/or the peeling force may be directed away from the surface at an angle. For example the example of angle of the peeling may range for example between 60-90 degrees and/or between 30-60 degrees and/or between 0 and 30 degrees. For example extenders 586a,b may optionally unfold and/or flex in such a way as to peel adhesive cover 589 bit by bit. Peeling may optionally be from an edge of adhesive 578 and/or towards the center.

Figure 5C:
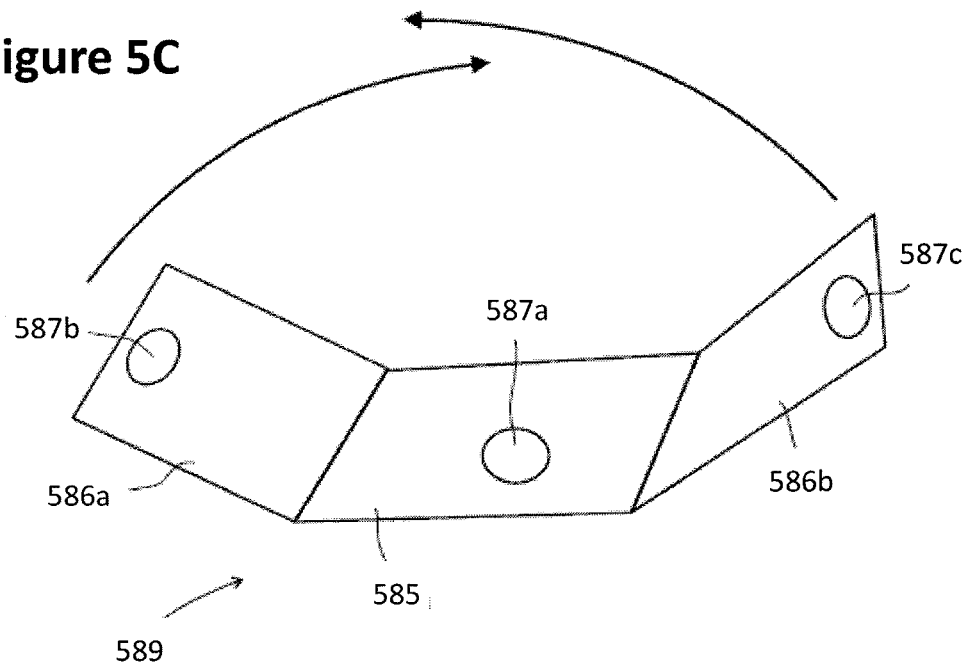
FIGS. 5C-D are schematic perspective view illustrations of a surface cover for shielding an active surface of a compound device according to an embodiment of the present invention.
Figure 5D:
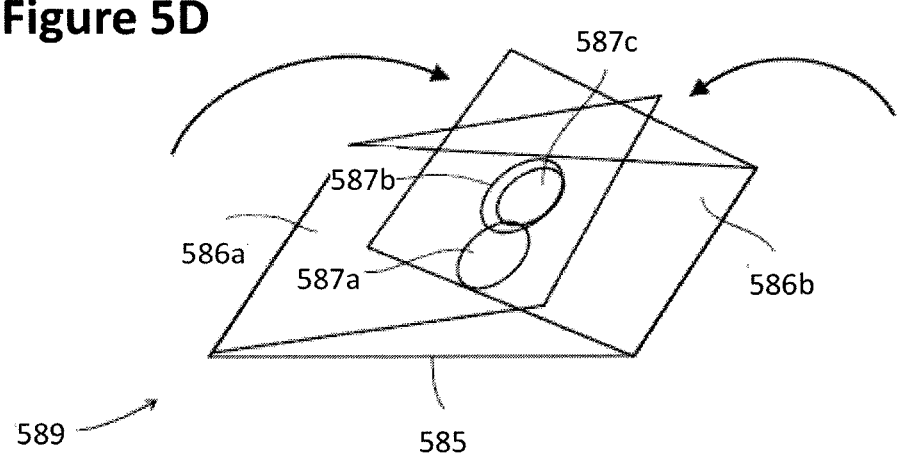

FIGS. 5C and 5D illustrate an exemplary method of forming extenders 586a,b from adhesive cover 589. For example, adhesive cover may include three folded portions including for example an adhered portion 585, and/or two extenders 586a,b. For example, adhesive cover may include three holes 587a,b,c. When folded, the extenders 586a,b may fold over the adhered portion 585. Holes 587b,c in extenders 586a,b may line up with hole 587a in adhered portion 585. In some embodiments, adhered portion 585 will be adhered to base 542 with the needle opening accessible through holes 587a-c. A cap (for example safety cap 592) may protrude through holes 587a-c. The cap may optionally be attached to portions 586b,c. The safety cap may pass freely through hole 587a and/or not be attached to portion 585 of adhesive cover 589.

FIGS. 5E-H illustrate removal of an exemplary safety cap 592, needle protector 591 and/or adhesive cover 589. For example, while safety cap 592 is mounted to needle protector 591, safety cap may prevent deployment and/or activation of the injector. For example, safety cap 592 and handle 594 may supply a convenient means of removing needle protector 591 and/or adhesive cover 589.

Figure 5E:
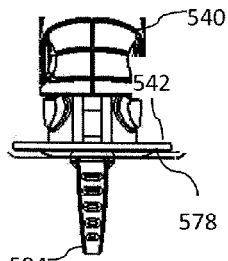
FIGS. 5E-H are a cross sectional illustrations of peeling a surface cover according to an embodiment of the present invention.

FIG. 5E illustrates injector 500 in a safe state for storage and/or transport. Needle protector 591, safety cap 592 and adhesive cover 589 are in place. Adhesive cover 589 is folded for example as illustrated in FIG. 5D. Needle protector 591 (not seen in the drawing) may optionally preserve the sterility of needle 560. Safety cap 592 may optionally surround and/or grasp needle protector 591. Safety cap 592 may prevent inadvertent activation of the injector and/or protect users from a needle stick hazard.

Figure 5F:
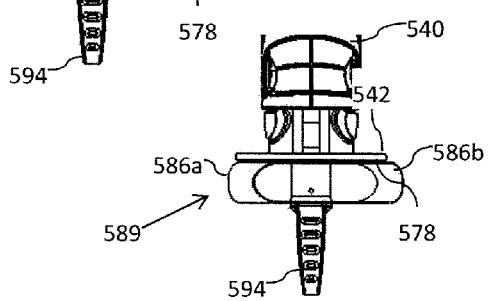

FIG. 5F illustrates the beginning of removal of safety cap 592. A user optionally pulls handle 594 away from needle 560. Handle 594 pulls needle protector 591 out the needle hole of injector 500 and through hole 587a. As cap 592 is pulled away from base 542, extenders 586a,b unfold while adhered portion 585 remains adhered to base 542.

Figure 5G:
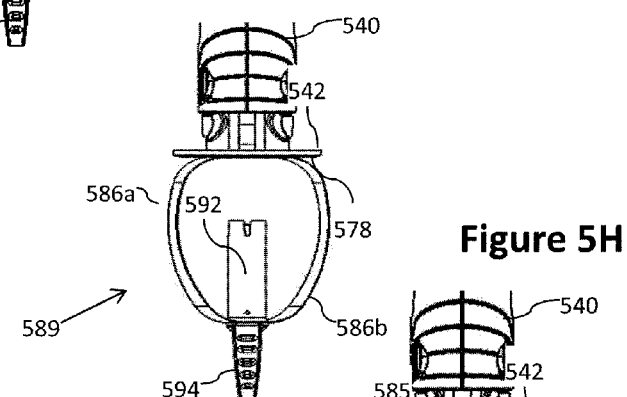

FIG. 5G illustrates that as safety cap 592 is pulled further away from base 542 extenders 586a,b pull and peel opposite edges of adhered portion 585 away from base 542. In some embodiments, pulling opposite edges of adhered portion 585 may balance the forces on safety cap 592. The balanced forces may produce a net force on cap 592 that is substantially perpendicular to base 542.

Figure 5H:
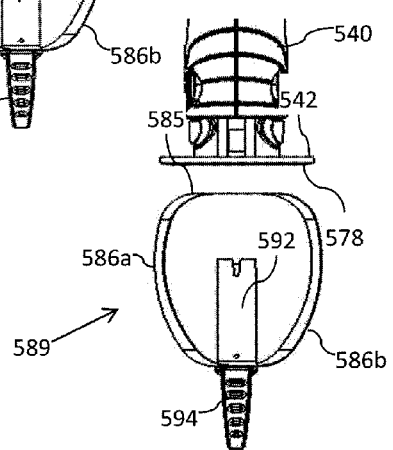

FIG. 5H illustrates safety cap 592 and adhesive cover 589 fully removed from injector 500, such that injector 500 is enabled and/or ready to adhere to a patient and/or ready for activation.

Figure 5I:
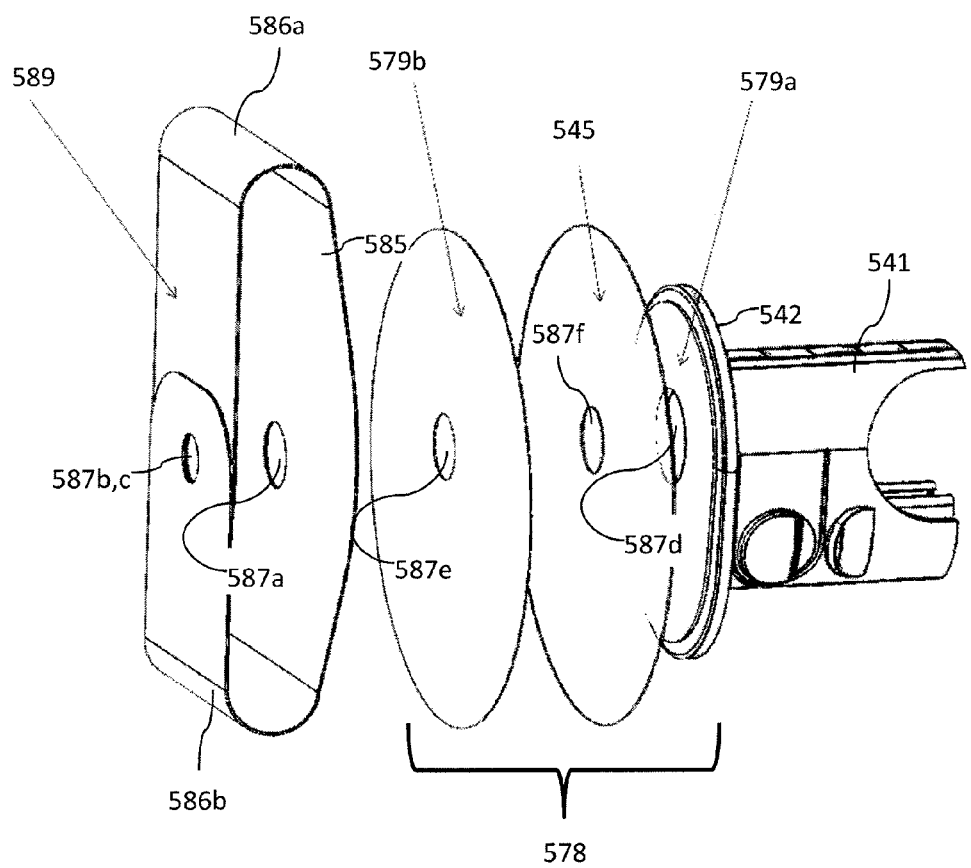
FIG. 5I is an exploded view illustrations of a surface cover according to an embodiment of the present invention.

FIG. 5I illustrates details of the structure of an active zone including an adhesive 578 formed on a surface according to some embodiments of the current invention. In some embodiments a wall of a device (for example base 542) may have an active surface (for example adhesive 578). Optionally the adhesive may be formed in layers. For example, as illustrated in FIG. 5I, adhesive 578 includes three layers. A first layer includes a dual sided adhesive 579a. Adhesive 579a may, for example, join a semi-stiff membrane 545 to base 542 Membrane 545 may extend beyond the edges of base 542. A semi-stiff extension beyond the edges of base 542 may in some embodiments make the injector adhere more strongly the skin of a user. A semi-stiff extension beyond the edges of base 542 may in some embodiments make it more difficult to peel adhesive cover 589 from adhesive 578. The angle of peeling of adhesive cover 589 and/or the stiffness of membrane 545 may be adjusted (for example the angle of peeling made shallower and/or the membrane made stiffer) to facilitate peeling adhesive cover 589 without undue bending of membrane 554. For example, the adhesive cover removal force may range between 10-150 gr/cm. The adhesive cover removal force may be lower than the bending inertia of the adhesive membrane 545. For example this may prevent bending of membrane 545 when removing the adhesive cover. An external face of membrane 545 may optionally include an active surface, for example an adhesive 579b. An active surface for the purpose of this application may be a surface that has active modality wherein the surface interacts with an external element facilitating the functioning of the device and an inactive modality wherein it substantially does not interact with the external element. For example, prior to enablement of injector 500 (for example see enabled 332 FIG. 3) adhesive 579b may be inactive and/or protected by adhesive cover 589. When the injector is active (for example, see active 333 FIG. 3) adhesive 579b may be actively interacting with a patient. For example adhesive 579b may adhere to the patient and/or support the injector on the patient. Alternatively or additionally, an active surface may include a drug for example an antiseptic and/or an anesthetic and/or an active surface may include a coupling agent for example a electrically conductive material, and/or an active surface may include an indicator material for example a pH sensitive dye and/or a heating material.

In some embodiments, a coupler (for example safety cap 592 see, for example, FIGS. 5A and 5G) may be used to open a seal of a protected enclosure (for example needle protector 591 for example see FIG. 5A) and/or surface cover 589. For example, after installing syringe 546 and/or needle 560 in a sterile state sealed by needle cover 591, a proximal end safety cap 592 may be inserted through holes 587e, 587f and 587d in adhesive 579b, membrane 545 and base 542 respectively. The proximal end of safety cap 592 may, for example, snap over and/or attach to needle cover 591. The distal end of safety cap 592 may, for example, remain protruding external to injector 500. Optionally, extenders 586a,b may be folded over and/or holes 587b,c may be attached to the distal end of safety cap 592. For example, extenders 586a,b may be clamped to the distal end of safety cap 592 using handle 594 (see for example FIGS. 5A, 5B, 5G).

Figure 5J:
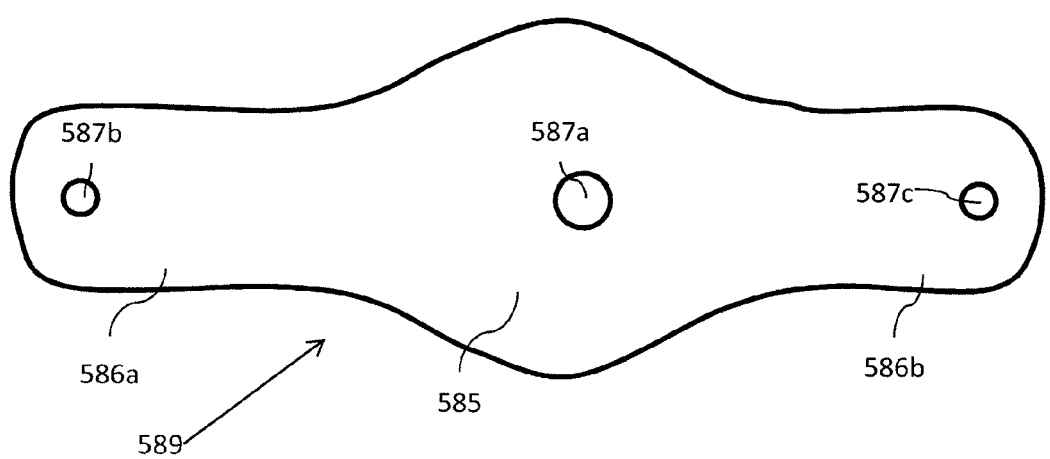
FIG. 5J is an orthogonal view illustrations of a surface cover according to an embodiment of the present invention.
Figure 5K:
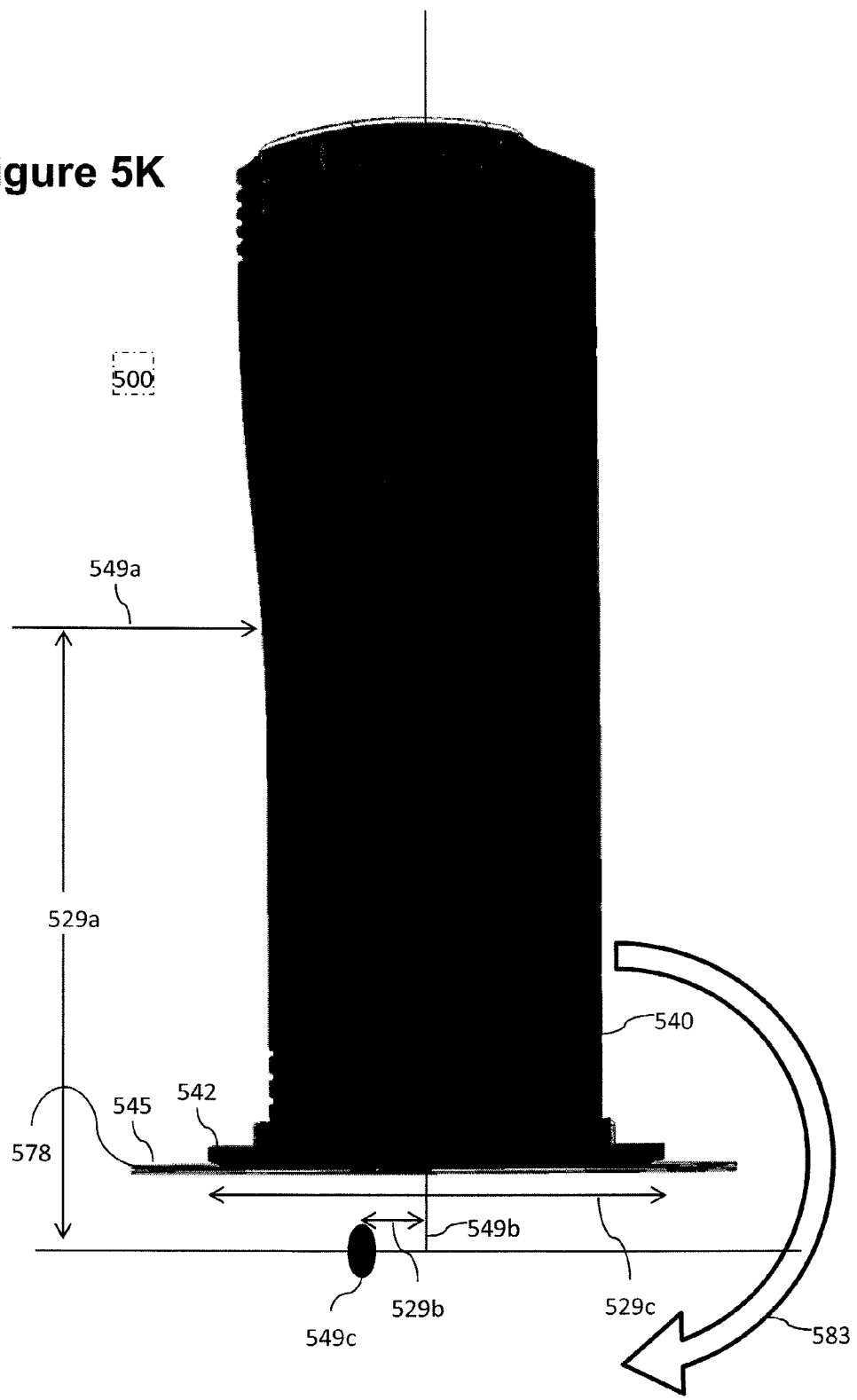
FIG. 5K is an orthogonal silhouette view of a stabilized injector according to an embodiment of the present invention.

FIG. 5J illustrates adhesive cover 589 spread out flat according to some embodiments of the current invention. In the embodiment of FIG. 5J, adhered portion 585 of cover 589 may optionally be wider than extenders 586a,b. For example, adhered portion 585 may have a width ranging 70±20 mm and extenders 586a,b may have a width ranging 30±10 mm. The length of each extender 586a,b may range for example 180±80 mm. Attachment holes 587b,c may have a diameter of for example 6±2 mm. Insertion hole 587a may have a diameter of for example 10±4 mm. Alternatively or additionally, holes 587a,b,c may be centered on the device and/or they may be off center. Cover 589 may optionally be made of and/or coated with an adhesive inert material.

FIG. 5J illustrates external dimensions of injector 500 according to some embodiments of the current invention. In some embodiments, the distance 529a from the longitudinal center of mass 549a of the injector and the adhesive surface 578 may range for example between 50±10 mm. The distance 529b between the lateral center of mass 549b of the injector and the center of adhesion 549c on base 542 of the apparatus (when the weighted center of force on the adhesive when the injector is twisted off the skin in the direction of the arrow 683 in FIG. 5K) may range, for example between 12.5±4 mm. The width 529c of base 542 may range, for example, between 60±15 mm. There may optionally be a semi-stiff skirt 545 extending between 0 and 20 mm beyond the edge of base 542. (For example the skirt may be made of plastic, for example Polyethylene terephthalate (PET) and/or Polycarbonate and/or ABS. The thickness of the skirt may range for example between 0.1 to 0.8 mm.). The thickness of adhesive layer 578 may range between 0.1 and 1 mm. An injector may weigh for example 50±20 g. Then the resting torque adhesive when the injector is adhered to a vertical object will be approximately 50 mm×50 g=2500 g×mm. The strength of adhesion necessary to hold the injector to the patient will be approximately 2500 g×mm/12.5 mm=200 g. In some embodiments, movements of the user may place a considerably stress on the injector than the static stress. For example an adhesive may be provided to give a total adhesive strength ranging between 500-1500 g.

In some embodiments, the adhesive will be less strong and/or maybe easier to remove. For example the strength of the adhesive may be less than 500 g (for example the user may have to hold the injector with his hand to prevent it from falling, especially when the user is moving). Alternatively or additionally the adhesive may not include semi-stiff skirt 545.

In some embodiments, the adhesive may include a semi stiff skirt. The skirt may make the injector more stable. Alternatively or additionally, the adhesive may be connected to a stiff base (for example the base of the injector) without a semi-stiff skirt. For example, an embodiment without a semi stiff skirt may be easier to remove after the end of injection.

Various aspects or features illustrated herein with respect to a particular embodiment may be combined with other alternative embodiments. For example, needle 560 of injector 500 is illustrated perpendicular to base 542. Alternatively or additionally, needle 560, may optionally be mounted at an acute angle to base 542. Needle protectors and/or protective covers may vary in geometry. Various retraction mechanisms may used, for example spring driven mechanism and/or clip and/or a screw driven rotary mechanism.

In some embodiments a syringe (for example syringe 546) may be preloaded with a medicine. For example the volume of preloading medicine may range between 0.5 and 1 ml and/or between 1 and 5 ml and/or greater than 5 ml of medicine. Preloading may optionally be performed on standard syringe equipment and using standard filling procedures. Optionally the syringe may be a standard type syringe. For example preloading may be done in an aseptic environment. In some embodiments, a syringe medicine container and/or needle may be filled and sealed under aseptic and/or sterile conditions, for example in an aseptic room. For example the syringe may be sealed by a needle protector and/or a plunger. Optionally, the syringe, with the fluid path in a sealed and/or protected state may be taken from the aseptic filling room and installed into an injector. Optionally, the fluid path may not require sterilization after being removed from the filling room and/or after installation into the injector. In some embodiments, the fluid path of the injector may include the medicine container and/or the needle. For example, in operation, medicine stored in the container may pass directly from the container to the needle and/or from the needle directly to the patient. Optionally, the entire fluid path may be in a complete and/or sterile and/or assembled and/or protected state prior to and/or during filling of the container.

6 Single Folded Surface Cover

Figure 6A:
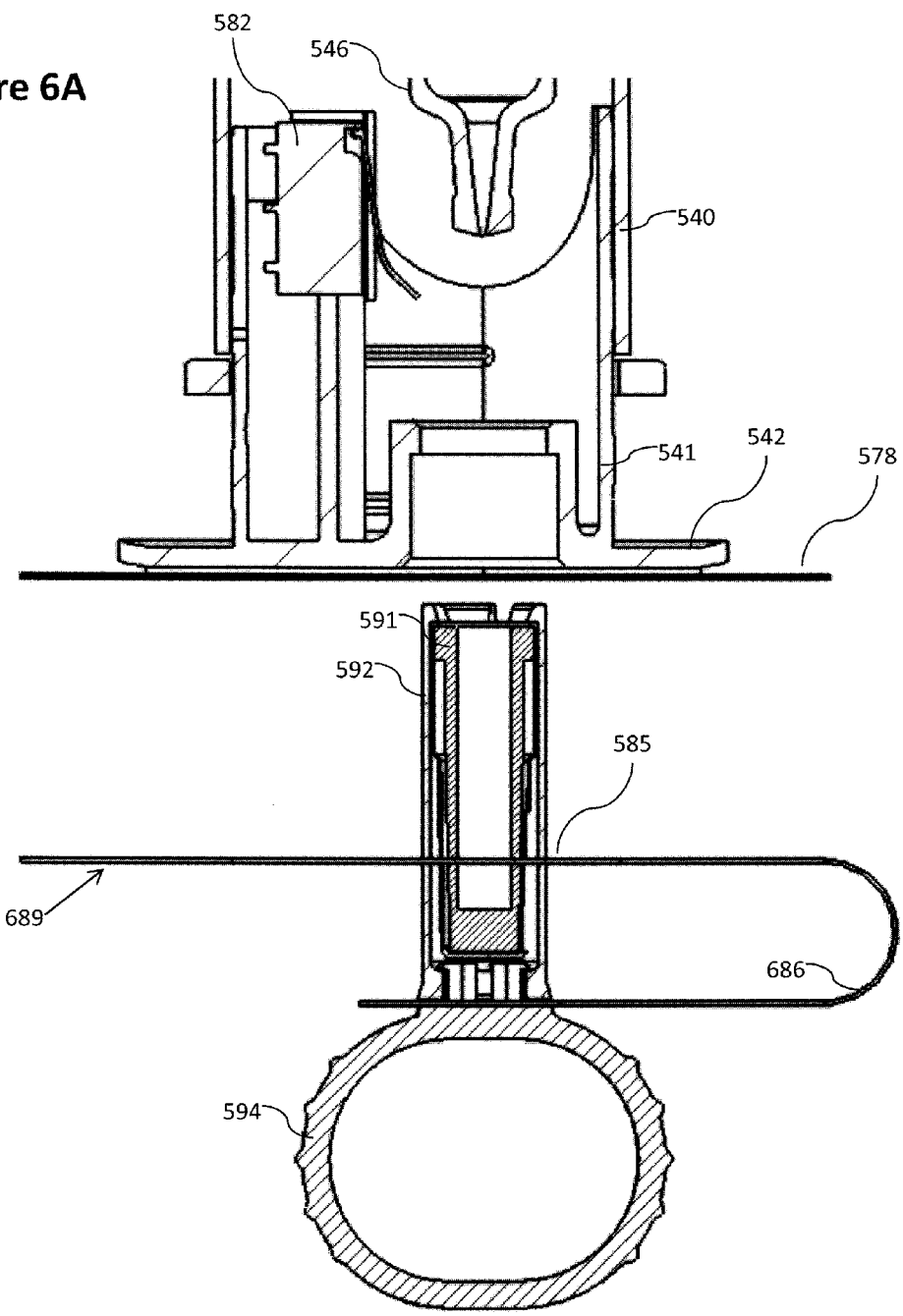
FIG. 6A is a cross sectional illustration of an alternative enabling assembly for a compound device according to an embodiment of the present invention.
Figure 6B:
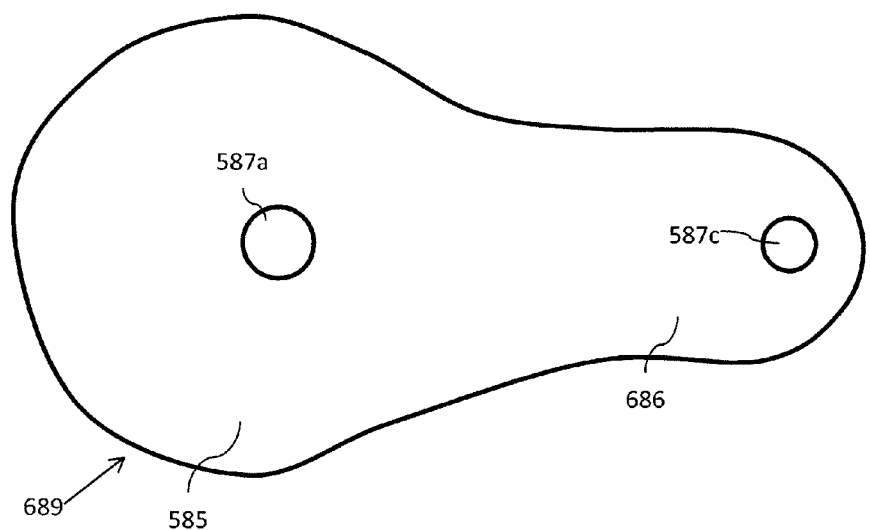
FIGS. 6B-C are schematic illustrations of an alternative surface cover for shielding an active surface of a compound device according to an embodiment of the present invention.
Figure 6C:
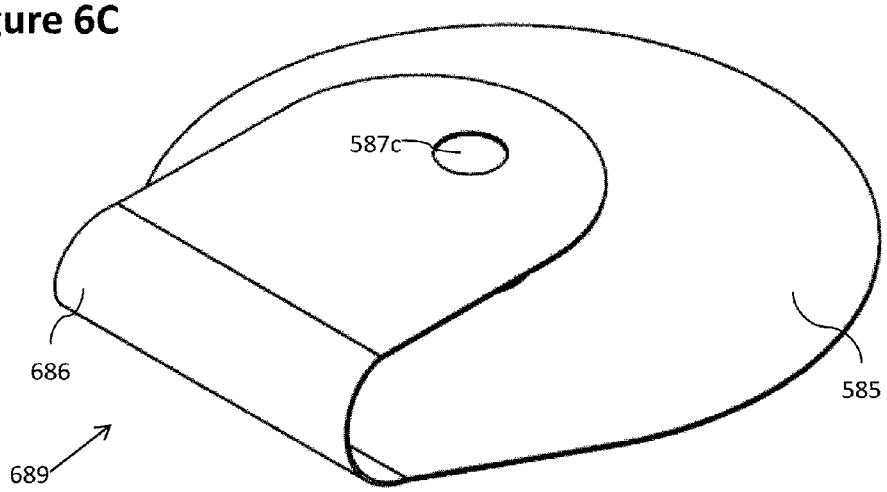

FIGS. 6A-C illustrate an alternate adhesive cover 689 having a single fold and/or extender according to some embodiments of the current invention. In FIGS. 6A-C, parts having similar geometry and function to counterparts in FIG. 5A-K are marked with the same number as their counterparts in FIGS. 5A-K. One difference between adhesive cover 689 and adhesive cover 589 is that adhesive cover 689 optionally includes a single extender 686. Extender 686 optionally peels adhered portion 685 from one edge and/or may not balance peeling forces.

FIG. 6A illustrates adhesive cover 689 attached to safety cap 592 according to some embodiments of the current invention. FIG. 5B illustrates adhesive cover 689 stretched out flat according to some embodiments of the current invention. FIG. 6C illustrates a perspective view of adhesive cover 689 in a folded state according to some embodiments of the current invention. Alternatively or additionally an adhesive cover may include three for or more extenders. Alternatively or additionally an adhered portion 585 may have a shape other than circular, for example oval, rectangular and/or irregular.

7, 8 and 9 Alternative Surface Covers

FIGS. 7A-D, and FIGS. 8, and 9 illustrate examples of alternate geometries for an adhesive cover peeler according to some embodiments of the current invention. An adhesive peeler may include for example extenders attached to an outer edge of a safety cap and/or may not include extenders and/or may include extenders from a central point on the safety cap.

Figure 7A:
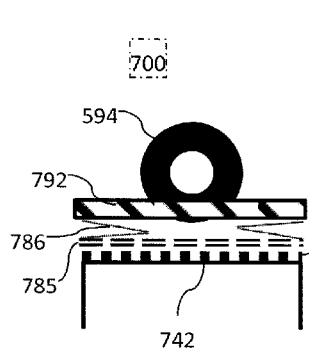
FIGS. 7A-C are a cross sectional illustrations of peeling an alternative surface cover according to an embodiment of the present invention.
Figure 7B:
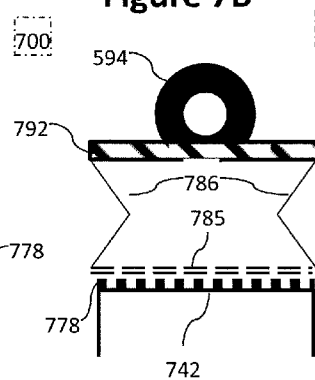
Figure 7C:
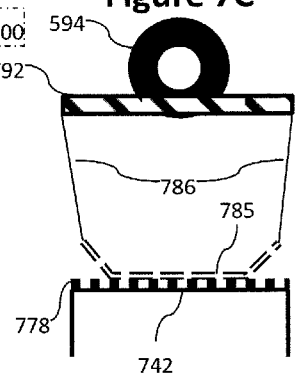

FIGS. 7A-C illustrated three stages of synchronized removal of a cap and peeling an adhesive cover according to some embodiments of the current invention. For example, a stiff cap 792 may cover an end 742 of a device 700. An active surface 778 may be formed on the outer surface of the device 700. In some embodiments, active surface 778 may be covered a protective cover 785. One or more extenders 786 may optionally join cap 792 to protective cover 785. For example in device 700, extenders 786 join the edges of cap 792 to the edges of protective cover 785. When cap 792 is closed onto surface 742, extenders 786 may optionally fold up (for example as illustrated in FIG. 7A). As cap 792 is pulled away from surface 742, extenders 786 may optionally unfurl (for example as illustrated in FIG. 7B). Pulling cap 792 further from surface 792 optionally peels cover 785 from surface 742 (for example as illustrated in FIG. 7C). As cover 785 peels off of surface 742 the lower ends of extenders 786 may be pulled inward and/or approach each other.

Figure 8:
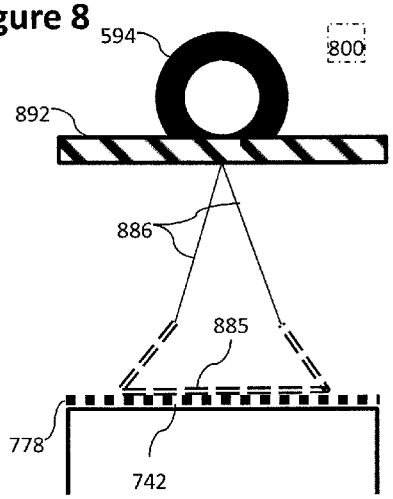
FIG. 8 is a cross sectional illustration of peeling an alternative surface cover according to an embodiment of the present invention.

FIG. 8 illustrates an alternate embodiment of synchronized removal of a cap and peeling an adhesive cover according to some embodiments of the current invention. For example, in device 800 of FIG. 8, extenders 886 join a central point of cap 892 to the edges of surface cover 885. As cover 892 is pulled away from surface 742, surface cover 885 is peeled from the active surface 778.

In some embodiments, extenders (for example 786 and/or 886) may be extensions of a surface cover (for example 785 and/or 885) (for example similar to extenders 586 illustrated in FIGS. 5A-K). For example, the extenders and the surface cover may be made of a flexible material. In some embodiments extenders may be a part of the cap. The cap and the extenders may be integrally formed of a single piece of flexible material. Alternatively or additionally, extenders may be formed separately from the cap and/or the surface cover. For example flexible extenders may be attached rigidly to the cap and/or the surface cover. Alternatively or additionally, extenders (whether the extenders are rigid and/or flexible) may be attached to the cap and/or the surface cover with a flexible attachment mechanism, for example a hinge and/or fold.

Figure 9:
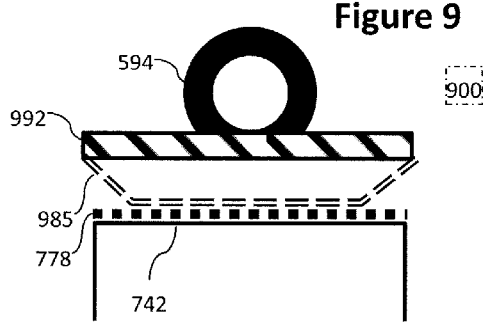
FIG. 9 is a cross sectional illustration of peeling an alternative surface cover according to an embodiment of the present invention.

FIG. 9 illustrates an alternate embodiment of synchronized removal of a cap and peeling an adhesive cover according to some embodiments of the current invention. For example, in device 900 of FIG. 9, the edges of a surface cover 985 are attached directly to a stiff cap 992 without extenders. As cap 992 is pulled away from surface 742, surface cover 985 is peeled from the active surface 778. Optionally, surface cover 985 may be elastic. The elasticity of cover 985 may optionally make it easier to distance cap 992 giving more leverage to the peeling. For example, as cover 985 is pulled away from surface 742, surface cover may stretch. As surface 742 surface cover may stretches, the angle between the raised ends of surface cover 985 and surface 742 may increase increases the leverage of the peeling force.

10 Patch Injector with Synchronized Unsealing and Surface Peeling

FIGS. 10A-D illustrate a compound device having synchronized removal of a seal and a surface cover according to some embodiments of the present invention. For example the a compound device may be a patch injector including for example a protected internal mechanism (for example an sterile injection needle sealed in an enclosure) and an active external surface (for example an adhesive surface). A surface protector covering may be joined to a seal of a needle enclosure. Peeling the surface protector may be synchronized with unsealing the protective enclosure.

Figure 10A:
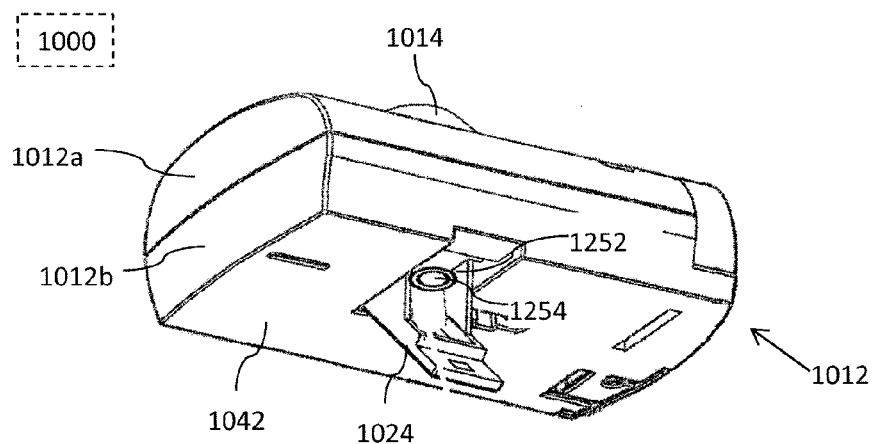
FIG. 10A illustrates an external perspective view of a patch injector according to an embodiment of the current invention.
Figure 10B:
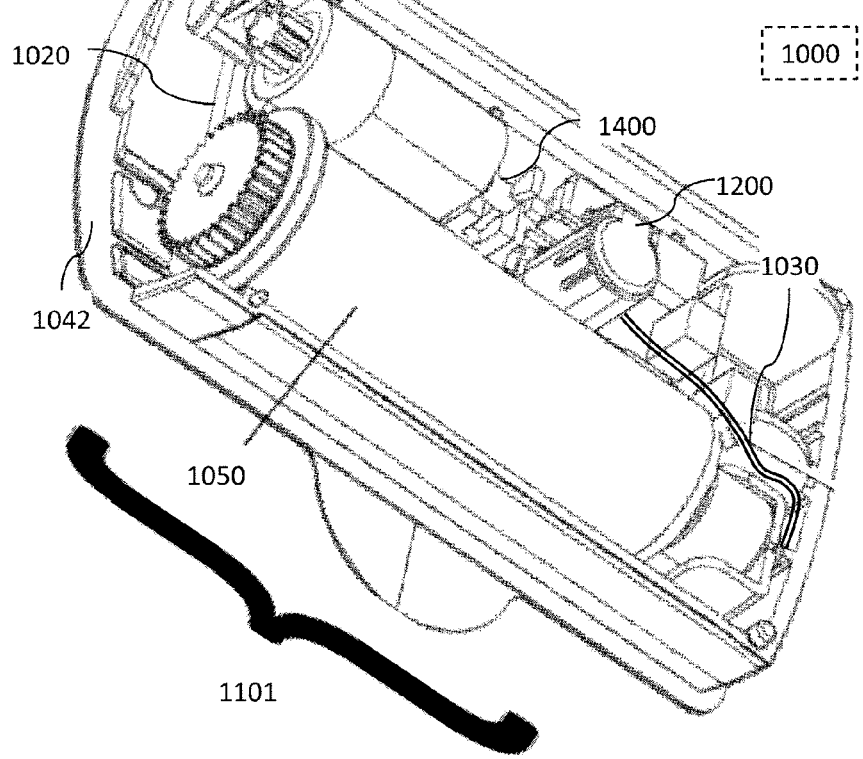
FIG. 10B illustrates a perspective view of the internal parts of a patch injector according to an embodiment of the current invention.

An exemplary patch injector, pump 1000 is, for example, a drug delivery systems capable of dispensing a fluid to a user upon activation. Such drug delivery systems include, for example, injection systems, infusion pumps, bolus injectors, and the like. FIGS. 10A and 10B show an exemplary drug delivery device according to at least one embodiment of the present invention. The drug delivery device may be utilized to administer delivery of a drug treatment into a body of a user. Drug pump 1000 may optionally include a pump housing 1012. Pump housing 1012 may include one or more housing subcomponents which are fixedly engageable to facilitate easier manufacturing, assembly, and operation of the drug pump. For example, drug pump 1000 includes a pump housing 1012 which includes an upper housing 1012a and a lower housing 1012b. Drug pump 1000 may further include an activation mechanism 1014. As shown in FIG. 10B, a drug pump may further include assembly platform 1020, drive mechanism 1101 having drug container 1050, insertion mechanism 1200, sterile fluid conduit 1030, and power and control system 1400. One or more of the components of such drug pumps may be modular in that they may be, for example, pre-assembled as separate components and configured into position onto the assembly platform 1020 of the drug pump 1000 during manufacturing.

Drug pump 1000 is configured such that, upon activation by a user by depression of activation mechanism 1014, the drug pump is initiated to: insert a fluid pathway into the user; enable, connect, and/or open necessary connections between a drug container, a fluid pathway, and a sterile fluid conduit; and/or force drug fluid stored in the drug container through the fluid pathway and fluid conduit for delivery into a user. One or more optional safety mechanisms may be utilized, for example, to prevent premature activation of the drug pump. For example, an optional on-body sensor 1024 may be provided in one embodiment as a safety feature to ensure that the power and control system 1400, and/or the activation mechanism, cannot be engaged unless the drug pump 1000 is in contact with the body of the user. In one such embodiment, the on-body sensor 1024 is located on the bottom of lower housing 1012b (for example on a patient contact surface 1042) where it may come in contact with the user's body. When the on-body sensor 1024 is depressed activation may optionally be permitted.

Figure 10C:
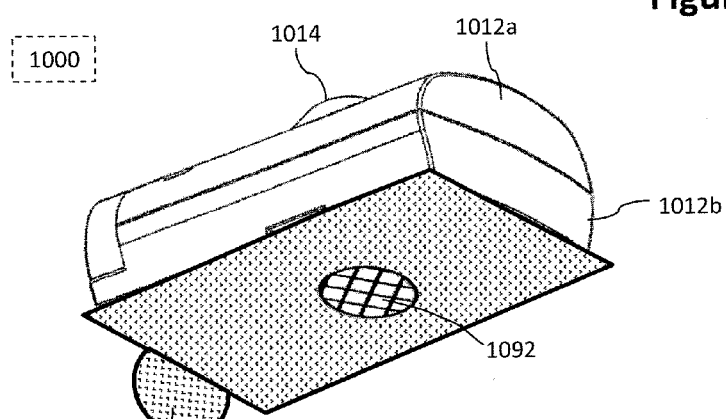
FIG. 10C illustrates an external perspective view of a patch injector including a surface cover and coupler according to an embodiment of the current invention.
Figure 10D:
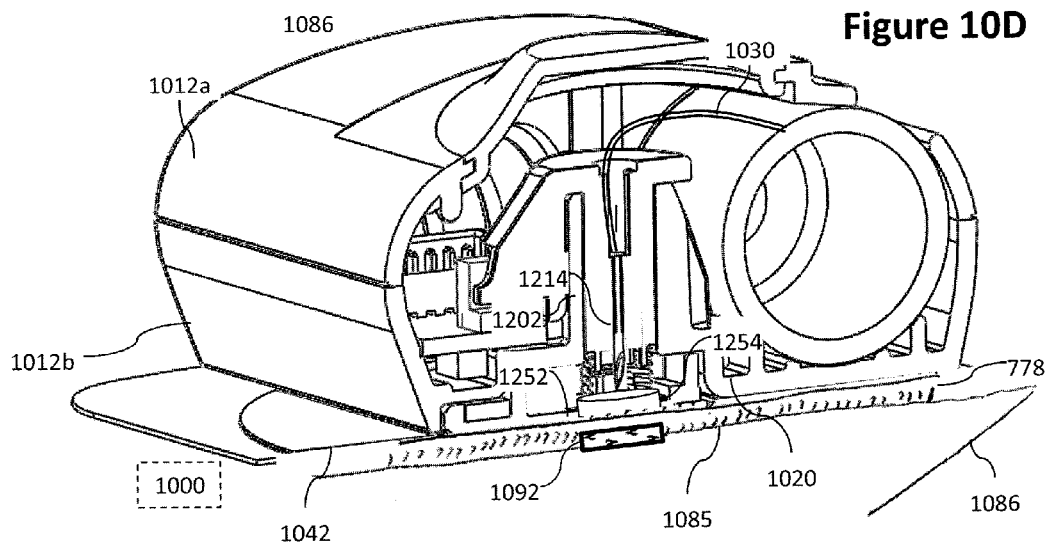
FIG. 10D illustrates a cross sectional view of enabling assembly of a patch injector according to an embodiment of the current invention.

In some embodiments, insertion mechanism 1200 may include a sterile enclosure 1202 (for example as illustrated in FIG. 10D) having a base 1252. Base 1252 may be connected to assembly platform 1020 to integrate the insertion mechanism into the drug pump 1000 (as shown for example in FIG. 10A). In some embodiments, the bottom of base 1252 may include a seal 1254 that, at least in one embodiment, is removable prior to use of the drug pump 1000. For example at least a part of the fluid path of pump 1000 may be produced and/or sealed in enclosure 1202. The assembled fluid path and/or sealed enclosure may be installed into housing 1012 as a complete component.

In some embodiments the insertion mechanism 1200 may further include, for example, an insertion biasing member and/or a needle 1214 (see for example FIG. 10D). Needle 1214 may optionally connect to sterile fluid conduit 1030 to permit fluid flow through needle 1214 and/or a cannula, and into the body of the user during drug delivery. Optionally, there may be a sterile septum under seal 1254. The septum may protect needle 1214 and/or keep it sterile until needle 1214 is inserted through the septum into a patient.

FIG. 10C illustrates a view of pump 1000 from the side of patient contact surface 1042. In some embodiments, after assembling insertion mechanism 1200 into pump 1000, an adhesive 778 layer (for example as illustrated in FIG. 10D) may be formed on and/or adhered onto an external side of patient contact surface 1042. Adhesive 778 may optionally be formed on and/or adhered onto an external surface of seal 1254. After forming the adhesive 778 layer, adhesive cover 1085 along with coupler 1092 may be placed over the adhesive. The adhesive may be protected from the external environment by surface cover 1085. Surface cover 1085 may be joined to seal 1254 by a coupler (for example coupler 1092 as illustrated for example in FIGS. 10C and 10D). In alternative embodiments, details of construction may differ, for example, adhesive may be formed on an external surface of drug delivery device before installation of insertion mechanism 1200.

According to some embodiments (for example in the exemplary embodiment of FIG. 10D), a user enables the injector by grasping a tab 1086 and peeling off adhesive cover 1085 with coupler 1092. Optionally, adhesive cover 1085 is made of an adhesive inert material. When adhesive cover 1085 is peeled off, adhesive 778 remains on most of the contact surface 1042. On the other hand, coupler 1092 may adhere via adhesive 778 and/or to seal 1254. When cover 1085 and/or coupler 1092 are peeled off, seal 1254 may be come off with coupler 1092. For example there may be a hole in on body sensor 1024 through which seal 1254 and coupler 1092 are connected.

FIGS. 11A-B illustrate an alternative synchronized system 1100 for peeling a surface protector and unsealing an enclosure according to some embodiments of the current invention. Optionally, system 1100 is compatible and/or may be used with a patch injector such as pump 1000. For example, after mounting needle insertion mechanism 1200, and outside surface of the device may be formed and/or adhered to a patient contact surface 1042. A surface cover 785 may be placed over adhesive 778 for example protecting adhesive 778 from the external environment. A hard cap 1192 may also be placed over the surface (for example as illustrated in FIG. 11A). Cap 1192 may be attached to surface cover 785 by extenders 1186. A handle 1194 may be inserted through a hole 1187 in cap 1192 and/or cover 785 and/or adhesive 778. Handle 1194 may be attached to seal 1154.

According to some embodiments (for example as illustrated in FIGS. 11A,B) a user enables a device by pulling handle 1194 away from surface 1042. Pulling handle may optionally pull up seal 1154. Seal 1154 may optionally be larger than hole 1187 in cap 1192. Pulling seal 1154 away from surface 1142 may also pull cap 1192 away. As cap 1192 is pulled away from surface 1042 extenders 1186 unfurl and/or peel surface protector 785 from surface 1142. For example, extenders 1186 may function in a manner similar to extenders 786 of FIG. 7A.

Figure 12A:
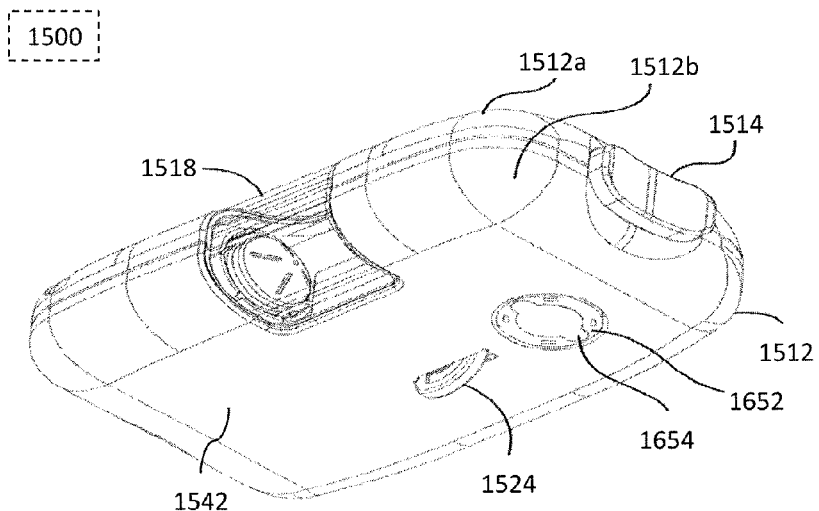
FIG. 12A illustrates an external perspective view of an alternative patch injector according to an embodiment of the current invention.
Figure 12B:
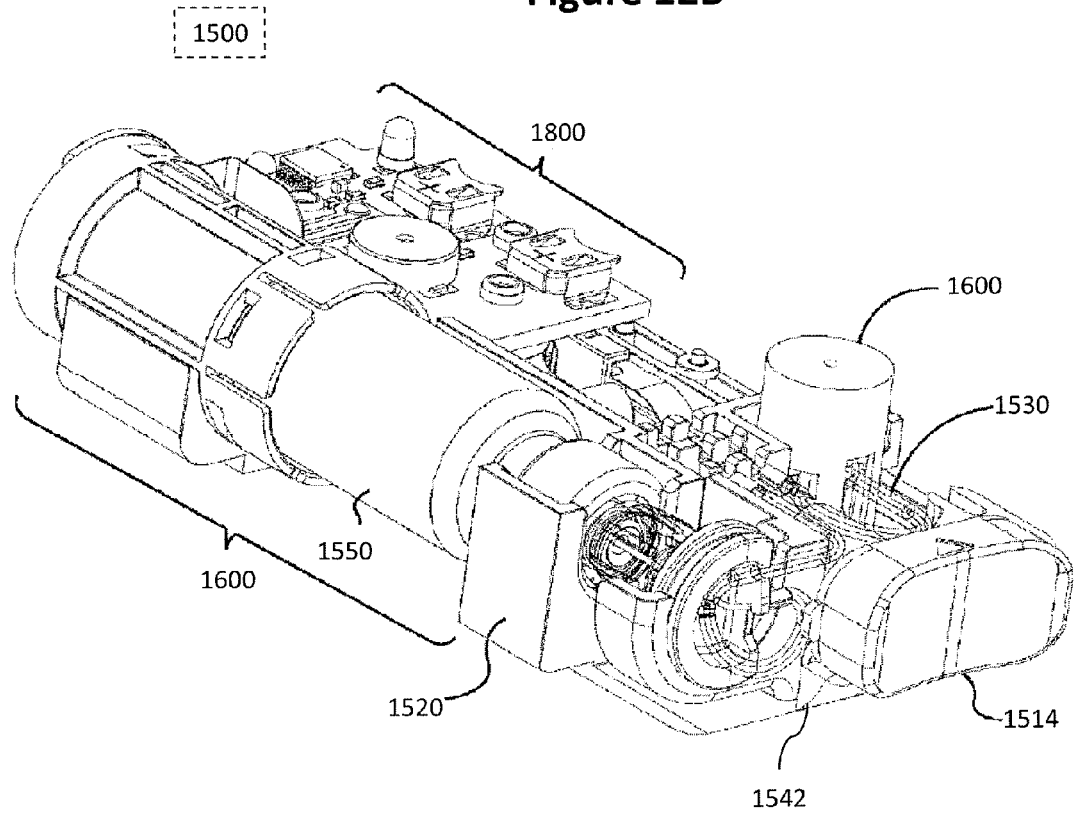
FIG. 12B illustrates a perspective view of the internal parts of an alternative patch injector according to an embodiment of the current invention.
Figure 12C:
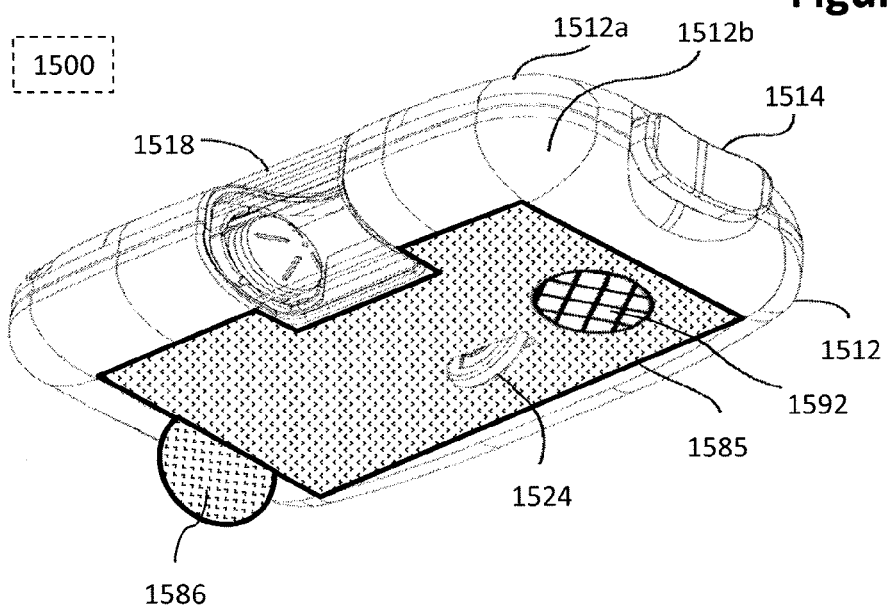
FIG. 12C illustrates an external perspective view of an alternative patch injector including a surface cover and coupler according to an embodiment of the current invention.

FIGS. 12A-C illustrate an alternative patch injector 1200 having synchronized removal of a seal and a surface cover according to some embodiments of the present invention.

An exemplary patch injector, pump 1500 is, for example, a drug delivery systems capable of dispensing a fluid to a user upon activation. Such drug delivery systems include, for example, injection systems, infusion pumps, bolus injectors, and the like. FIGS. 12A and 12B show an exemplary drug delivery device according to at least one embodiment of the present invention. The drug delivery device may be utilized to administer delivery of a drug treatment into a body of a user. Drug pump 1500 may optionally include a pump housing 1512. Pump housing 1512 may include one or more housing subcomponents which are fixedly engageable to facilitate easier manufacturing, assembly, and operation of the drug pump. For example, drug pump 1500 includes a pump housing 1512 which includes an upper housing 1512a and a lower housing 1512b. Drug pump 1500 may further include an activation mechanism 1514, and a window 1518. Window 1518 may be any translucent or transmissive surface through which the operation of the drug pump may be viewed. As shown in FIG. 12B, drug pump further includes assembly platform 1520, sterile fluid conduit 1530, drive mechanism 1600 having drug container 1550, insertion mechanism 1600, fluid pathway connection 1530, and power and control system 1800. One or more of the components of such drug pumps may be modular in that they may be, for example, pre-assembled as separate components and configured into position onto the assembly platform 1520 of the drug pump 1500 during manufacturing.

Drug pump 1500 is configured such that, upon activation by a user by depression of activation mechanism 1514, the drug pump is initiated to: insert a fluid pathway into the user; enable, connect, and/or open necessary connections between a drug container, a fluid pathway, and a sterile fluid conduit; and/or force drug fluid stored in the drug container through the fluid pathway and fluid conduit for delivery into a user. One or more optional safety mechanisms may be utilized, for example, to prevent premature activation of the drug pump. For example, an optional on-body sensor 1524 may be provided in one embodiment as a safety feature to ensure that the power and control system 1400, and/or the activation mechanism, cannot be engaged unless the drug pump 1500 is in contact with the body of the user. In one such embodiment, the on-body sensor 1524 is located on the bottom of lower housing 1512*b* (for example on a patient contact surface 1542) where it may come in contact with the user's body. Upon displacement of the on-body sensor 1524, depression of the activation mechanism is permitted.

In some embodiments, insertion mechanism 1600 may include a sterile enclosure 1202 having a base 1652. Base 1652 may be connected to assembly platform 1520 to integrate the insertion mechanism into the drug pump 1500 (as shown for example in FIG. 12A). The connection of the base 1652 to the assembly platform 1520 may be, for example, such that the bottom of the base is permitted to pass-through a hole in the assembly platform to permit direct contact of the base to the body of the user. In some embodiments, the bottom of base 1652 may include a seal 1654 that, at least in one embodiment, is removable prior to use of the drug pump 1500. For example at least a part of the fluid path of pump 1500 may be produced and/or sealed in enclosure 1602. The assembled fluid path and/or sealed enclosure may be installed into housing 1612 as a complete component.

In some embodiments the insertion mechanism 1600 may further include, for example, an insertion biasing member and/or a needle 1614. Needle 1614 may optionally connect to sterile fluid conduit 1530 to permit fluid flow through needle 1614 and/or a cannula, and into the body of the user during drug delivery. Optionally, there may be a sterile septum under seal 1654. The septum may protect needle 1614 and/or keep it sterile until needle 1614 is inserted through the septum into a patient.

FIG. 12C illustrates a view of pump 1500 from the side of patient contact surface 1542. In some embodiments, after assembling insertion mechanism 1600 into pump 1500, an adhesive 778 layer (for example as illustrated in FIG. 12D) may be formed on and/or adhered onto an external side of patient contact surface 1542. Adhesive 778 may optionally be formed on and/or adhered onto an external surface of seal 1554. After forming the adhesive 778 layer, adhesive cover 1585 along with coupler 1592 may be placed over the adhesive. The adhesive may be protected from the external environment by surface cover 1585. Surface cover 1585 may be joined to seal 1654 by a coupler (for example connector 1592 as illustrated for example in FIGS. 12C and 12D). In alternative embodiments, details of construction may differ, for example, adhesive may be formed on an external surface of drug delivery device before installation of insertion mechanism 1600.

According to some embodiments (for example in the exemplary embodiment of FIG. 12D), a user enables the injector by grasping a tab 1586 and peeling off adhesive cover 1585 with coupler 1592. Optionally, adhesive cover 1585 is made of an adhesive inert material. When adhesive cover 1585 is peeled off, adhesive 778 remains on most of the contact surface 1542. On the other hand, coupler 1592 may adhere via adhesive 778 and/or to seal 1652. When cover 1585 and/or coupler 1592 are peeled off, seal 1652 may be come off with coupler 1592.

It is expected that during the life of a patent maturing from this application many relevant technologies will be developed and the scope of the terms are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound device having an interior volume and an exterior surface comprising:
   a wall located between the interior volume and an exterior of the compound device;
   a protected component surrounded by an enclosure, said enclosure at least partially located in the interior volume;
   a seal for closing said enclosure and isolating said protected component from said wall and for sealing the protected component from atmosphere;
   an active area formed on at least a portion of the exterior surface;
   a cover shielding said active area from said exterior; and,
   a coupler attaching said seal to said cover, such that withdrawal of said coupler away from said active area synchronizes removal of said cover and unsealing of said enclosure.

2. The compound device of claim 1, further comprising an opening in said wall exposing said enclosure to said exterior.

3. The compound device of claim 2, wherein said active area is adjacent to said opening.

4. The compound device of claim 2, wherein said coupler connects said seal to said cover via said opening.

5. The compound device of claim 1, wherein said active area includes an adhesive and said cover shields said adhesive from said exterior.

6. The compound device of claim 1, wherein said protected component includes a hypodermic needle.

7. The compound device of claim 6, wherein said seal includes a needle protective sleeve and wherein said unsealing includes removing said sleeve.

8. The compound device of claim 6, further comprising an opening in said wall exposing said enclosure to said exterior and wherein said hypodermic needle is directed to protrude through said opening in said wall.

9. The compound device of claim 1, wherein said coupler converts a movement away from the exterior surface into a peeling force on said cover.

10. The compound device of claim 1, wherein said coupler is connected to an edge of said cover.

11. The compound device of claim 1, wherein a volume of said enclosure is smaller than a volume of said interior volume.

12. A method of preparing a device for use, the device including an active outer surface and a protected component isolated from a wall of the device and sealed from atmosphere by a sealed enclosure; the active outer surface protected by a surface cover and a coupler attaching said sealed enclosure to said cover, the method comprising:
   withdrawing said coupler away from said active outer surface, and, in turn
   activating the active outer surface by removing the surface cover and exposing the protected component to the wall of the device by unsealing the sealed enclosure in a synchronized manner.

13. The method of claim 12, wherein said activating includes peeling the surface cover from the active outer surface.

14. The method of claim 13, further comprising:
   pulling said coupler away from the surface cover to form a space prior to said peeling.

15. The method of claim 13, wherein the peeling force is applied on an edge of said cover.

16. The method of claim 12, wherein said unsealing includes pulling a needle protective sleeve along an axis of a needle.

17. The method of claim 12, wherein the protected component includes a hypodermic needle, the method further comprising:
   projecting said hypodermic needle through an opening in the wall.

18. The method of claim 17, wherein said peeling includes peeling said surface cover from said active surface adjacent to said opening.

19. A compound device having an interior volume and an exterior surface comprising:
   a wall located between the interior volume and an exterior of the compound device;
   a protected component surrounded by an enclosure, said enclosure at least partially located in the interior volume;
   an adhesive layer on at least a portion of the exterior surface;
   a surface cover shielding said adhesive layer from said exterior;
   a hard cap placed over the surface cover and being attached thereto;
   a seal for closing said enclosure, isolating said protected component from said wall and sealing the protected component from atmosphere; and,
   a coupler attached to said seal,
   wherein withdrawal of said coupler away from said adhesive layer withdraws said seal from said enclosure and engages said seal with said hard cap, to, in turn, withdraw said hard cap away from said adhesive layer, thereby peeling the surface cover from the adhesive layer.

20. The compound device of claim 19, wherein the coupler extends through the surface cover and the hard cap and into engagement with the seal, the hard cap defining an aperture and the seal being greater in size than said aperture.

21. The compound device of claim 20, wherein the surface cover defines an aperture greater in size than the hard cap aperture and greater in size than the seal, the surface cover aperture overlapping with the hard cap aperture.

22. The compound device of claim 20, wherein the coupler comprises a handle and an extension extending therefrom, through the surface cover and the hard cap and into engagement with the seal, the hard cap and the surface cover being sandwiched between the handle and the seal, the hard cap being proximate the handle and the surface cover being proximate the seal.

23. The compound device of claim 19, wherein the hard cap comprises at least one member extending therefrom and attached to the surface cover, and withdrawal of said hard cap away from said adhesive layer unfurls said at least on member and peels the surface cover from the adhesive layer.

* * * * *